US007741022B2

(12) United States Patent
Porter et al.

(10) Patent No.: US 7,741,022 B2
(45) Date of Patent: Jun. 22, 2010

(54) PROTEIN INHIBITOR OF RAN ACTIVITY AND METHODS OF USE THEREOF

(75) Inventors: Frederick William Porter, Monona, WI (US); Ann Carol Palmenberg, Madison, WI (US); Christiane Wiese, Madison, WI (US); Yury Alexandrovitch Bochkov, Madison, WI (US)

(73) Assignee: Wisconsin Alumi Research Foundation, Madison, WI (US)

(*) Notice: Subject to any disclaimer, the term of this patent is extended or adjusted under 35 U.S.C. 154(b) by 0 days.

(21) Appl. No.: 11/654,848

(22) Filed: Jan. 18, 2007

(65) Prior Publication Data

US 2007/0243169 A1 Oct. 18, 2007

Related U.S. Application Data

(60) Provisional application No. 60/760,248, filed on Jan. 20, 2006, provisional application No. 60/743,139, filed on Jan. 18, 2006.

(51) Int. Cl.

*C12Q 1/00* (2006.01)

*A61K 38/00* (2006.01)

(52) U.S. Cl. .......................................... 435/4; 530/324

(58) Field of Classification Search ....................... None

See application file for complete search history.

(56) References Cited

OTHER PUBLICATIONS

Porter et al. Proceedings from the National Academies of Science, Aug. 15, 2006;103(33):12417-22. Epub Aug. 3, 2006.*

Lidsky, P.V.; Nucleocytoplasmic Traffic Disorder Induced by Cardioviruses; Journal of Virology, 2006; p. 2705-2717.

Dvorak, C.M.T.; Leader Protein of Encephalomyocarditis Virus Binds Zinc, Is Phosphorylated during Viral Infection, and Affects the Efficiency of Genome Translation; Virology, 2001; p. 261-271.

Porter, F.W.; A Picornavirus Protein Interacts with Ran-GTPase and Disrupts Nucleocytoplasmic Transport; PNAS, 2006; p. 12417-12422.

Delhaye, S.; The Leader Protein of Theiler's Virus Interferes with Nucleocytoplasmic Trafficking of Cellular Proteins; Journal of Virology, 2004; p. 4357-4362.

Belov, G.A.; Bidirectional Increase in Permeability of Nuclear Envelope upon Polivirus Infection and Accompanying Alterations of Nuclear Pores; Journal of Virology, 2004; p. 10166-10177.

* cited by examiner

*Primary Examiner*—Suzanne M. Noakes

(74) *Attorney, Agent, or Firm*—Quarles & Brady LLP

(57) ABSTRACT

The invention provides a method of inhibiting Ran protein activity in at least one eukaryotic cell or cell-free extract, the method comprising exposing an amino acid sequence comprising at least a portion of EMCV or TMEV leader protein, wherein the amino acid sequence comprises SEQ. ID NO: 14 or SEQ. ID NO: 15, to at least one cell in an amount effective to inhibit Ran activity in the targeted cell and evaluating Ran protein activity in the cell.

11 Claims, 11 Drawing Sheets
(5 of 11 Drawing Sheet(s) Filed in Color)

FIG. 6

```
align posit 1        .        .        .        .        .        .        .        80
                                                                                         SEQ ID NO
   vilyuisk  MA.......CkHgy.pdvCPiCtAidvtpgFeYLLlaDgEWfPtdLLcvDldDDVFwpsdssnqsatmewtDipLicdtVmEpQ  9
   tme-gd7b  MA.......CkHgy.pdvCPiCtAvdatpdFeYLLmaDgEWfPtdLLcvDldDDVFwpsdtstqpatmewtDvpLvcdtVmEpQ  10
    tme-gd7  MA.......CkHgy.pdvCPiCtAvdatpdFeYLLmaDgEWfPtdLLcvDldDDVFwpsdtstqpqtmewtDvpLvcdtVmEpQ  10
     tme-da  MA.......CkHgy.pdvCPiCtAvdvtpgFeYLLlaDgEWfPtdLLcvDldDDVFwpsnssnqsetmewtDlpLvrdiVmEpQ  11
   tme-bean  MA.......CkHgy.pdvCPiCtAvdatpdFeYLLmaDgEWYPtdLLcvDldDDVFwpsdtsnqsatmdwtDvpLirdiVmEpQ  12
tiv-ngs910   MA.......CiHgy.psvCPiCtAidkssdgmYLLlaDnEWfPadLLtmDldDDVFwpndesdvsetmdwtDlpfildtimEpQ  13
      emc-r  MATTMEQETCAHSLTFEECPKCSALQYRNGF.YLLKYDEEWYPEELL.TDGEDDVF..............DPELDMEVVFELQ  1
   emc-pv21  MATTMEQETCAHSLTFEECPKCSALQYRNGF.YLLKYDEEWYPEELL.TDGEDDVF..............DPELDMEVVFELQ  1
     emc-c4  MATTMEQETCAHSLTFEECPKCSALQYRNGF.YLLKYDEEWYPEELL.TDGEDDVF..............DPELDMEVVFELQ  1
    emc-bel  MATTMEQETCAHSLTFEECPKCSALQYRNGF.YLLKYDEEWYPEELL.iDGEDDVF..............DPELDTEVVFELQ  2
     emc-bd  MATTMEQEiCAHSLTlkgCPKCSALQYRNGF.YLLKYDEEWYPEELL.TDGEDDVF..............DPELDMEVVFELQ  3
     emc-bc  MATTMEQEiCAHSLTlkgCPKCSALQYRNGF.YLLKYDEEWYPEELL.TDGEDDVF..............DPELDMEVVFELQ  3
    emc-dvl  MATTMEQEiCAHSLTlkgCPKCSALQYRNGF.YLLKYDEEWYPEELL.TDGEDDVF..............DPELDMEVVFELQ  3
    emc-pv2  MATTMEQEiCAHSLTFkgCPKCSALQYRNGF.YLLKYDEEWYPEELL.TDGEDDVF..............DPELDMEVVFELQ  4
     emc-dd  MATTMEQEiCAHSLTFkgCPKCSALQYRNGF.YLLKYDEEWYPEELL.TDGEDDVF..............DPELDMEVVFELQ  4
     emc-dc  MATTMEQEiCAHSLTFkgCPKCSALQYRNGF.YLLKYDEEWYPEELL.TDGEDDVF..............DPELDMEVVFELQ  4
   emc-mn30  MATTMEQEiCvHSLiFEECPKCSALQYRdGF.YLLrYDEEWYPgELL.TDGEDDVF..............DPELDMEVVFELQ  5
    rz-pmwt  MATTMEQEiCAHSmTFEECPKCSALQYRNGF.YLLKYDEEWYPEELL.TDGEDDVF..............DPdLDMEVVFEtQ  6
    mengo-m  MATTMEQEiCAHSmTFEECPKCSALQYRNGF.YLLKYDEEWYPEEsL.TDGEDDVF..............DPdLDMEVVFEtQ  7
  mengo-37a  MATTMEQEiCAHSmTFEECPKCSALQYRNGF.YLLKYDEEWYPEELL.TDGEDDVF..............DPdLDiEVVFEtQ  8
```

PROTEIN INHIBITOR OF RAN ACTIVITY AND METHODS OF USE THEREOF

CROSS-REFERENCE TO RELATED APPLICATIONS

This application claims the benefit of U.S. provisional application 60/760,248, filed Jan. 20, 2006 and 60/743,139, filed Jan. 18, 2006. These applications are incorporated by reference as if fully set forth herein.

STATEMENT REGARDING FEDERALLY SPONSORED RESEARCH OR DEVELOPMENT

This invention was made with United States government support awarded by the following agencies: NIH, Grant Number AI07331; NSF, Grant Number 0344723. The United States government has certain rights in this invention.

BACKGROUND OF THE INVENTION

The eukaryotic nucleus provides a unique environment to separate DNA replication, transcription, and RNA processing events from protein synthesis in the cytoplasm. Communication between the nucleus and the cytoplasm occurs through massive nuclear pore complexes (NPCs) that span the nuclear envelope (NE). Protein or RNA transport in either direction is signal-dependent and requires interaction with an extended family of importin β-related receptors to chaperone the traffic (Stewart, M. L., Baker, R. P., Bayless, R., Clayton, L., Or ant, R. P., Littlewood, T & Matsuura, Y. (2001) *FEBS Lett.* 498, 145-149). Cargo association with these receptors is regulated by the type of guanine nucleotide (GTP or GDP) bound to the small GTPase, Ran (Gorlich, D. & Kutay, U. (1999) *Annu. Rev. Cell Dev. Biol.* 15, 607-660; Adam, S. A., Marr, R. S. & Gerace, L. (1990) *J. Cell Biol.* 111, 807-816). Cytoplasmic Ran is GDP-bound, whereas the GTP form predominates in the nucleus. There is a steep concentration gradient of the respective pools across the NPC. During interphase of the cell cycle, the gradient is maintained by Ran-associated factors separated by the NE (Gorlich, D. & Kutay, U. (1999) *Annu. Rev. Cell Dev. Biol.* 15, 607-660). Guanine nucleotide exchange factor RCC1 is exclusively nuclear and promotes RanGDP/GTP exchange. In the cytoplasm, RanGAP and RanBP1 accelerate the intrinsic slow rate of RanGTP hydrolysis, cycling the complex back to the GDP form (Bischoff, F. R., Klebe, C., Kretschmer, J., Wittinghofer, A. & Ponstingl, H. (1994) *Proc. Natl. Acad. Sci. USA* 91, 2587-2591). Cytoplasmic RanGDP has a low affinity for importin β, allowing the free form of the receptor to bind cargo and traffic through the NPC (Weis, K., Ryder, U. & Lamond, A. I. (1996) *EMBO J.* 15, 1818-1825). Inside the nucleus, higher-affinity RanGTP releases the cargo, then escorts the receptor back to the cytoplasm for another cycle (Gorlich, D., Pante, N., Kutay, U., Aebi, U. & Bischoff, F. R. (1996) *EMBO J.* 15, 5584-55 94). If GTP hydrolysis is inhibited, importin β remains bound to RanGTP and unavailable for active protein import. Without import, export of mRNA and ribosomal subunits are also inhibited because these processes require continuous nuclear reuptake of proteins that comprise export-competent ribonucleoproteins (RNPs) (Gorlich, D. & Kutay, U. (1999) *Annu. Rev. Cell Dev. Biol.* 15, 607-660). Therefore, if the Ran gradient fails, only proteins small enough to diffuse through the NPC (<40-60 kDa) can exchange.

The metabolic bottleneck posed by nuclear trafficking makes the NPC and associated processes vulnerable to attack by viruses intent on impeding signal transduction to the nucleus. NPC abrogation can prevent up-regulation of antiviral genes and the export of detrimental cellular mRNAs or enhance the redistribution of nuclear proteins required for viral replication (Belov, G. A., Lidsky, P. V., Mitkitas, O. V., Egger, D., Lukyanov, K. A., Bienz, K. & Agol, V. (2004) *J. Virol* 78, 10166-10177.). The family of RNA Picornavirus includes a variety of pathogenic agents. Among the better known members are poliovirus, rhinovirus, and foot-and-mouth disease virus. Others include the Coxsackie viruses, hepatitis A, swine vesicular disease, and cardioviruses like Mengo virus, encephalomyocarditis virus (EMCV), and Theiler's murine encephalomyelitis virus (Palmenberg, A. C. (1987) in *Positive Strand RNA Viruses*, eds. Brinton, M. A. & Rueckert, R. R. (Liss, New York), pp. 25-34.). These positive-sense RNA genomes direct a life cycle that is predominantly cytoplasmic and, indeed, can be recapitulated in a test tube in the absence of nuclei (Molla, A., Paul, A V. & Wimmer, E (1991) *Science* 254, 1647-1651.). During infection, however, Picornaviruses are adept at subverting innate cellular immunity traps, crippling the capacity of the cell to mount a defense. Within 2-3 h, infection brings to a halt all cellular mRNA transcription, cap-dependent mRNA translation, antiviral signal transduction, and active protein/RNA exchange between the nucleus and cytoplasm. The shutoff is profound. The viruses replicate with fecundity, and the cell dies before it ever triggers an alarm. Among the molecular processes involved in shutoff, poliovirus and rhinovirus encode a protease, $2A^{pro}$, which attacks nucleoporins within the NPC (Belov, G. A., Lidsky, P. V., Mitkitas, O. V., Egger, D., Lukyanov, K. A., Bienz, K. & Agol, V. (2004) *J. Virol* 78, 10166-10177; Gustin, K. E. & Sarnow, P. (2002) *J. Virol.* 76, 8787-8796; Gustin, K. E. & Sarnow, P. (2001) *EMBO J.* 20, 240-249). When visualized by electron microscopy, a "bar-like" structure spanning normal NPC channel is found to be missing (Belov, G. A., Lidsky, P. V., Mitkitas, O. V., Egger, D., Lukyanov, K. A., Bienz, K. & Agol, V. (2004) *J. Virol* 78, 10166-10177), and its absence correlates with an onset of unregulated efflux of small proteins from the nucleus into the cytoplasm.

Cardioviruses like EMCV also abrogate nucleocytoplasmic trafficking, but their genomes lack a 2A protease and instead encode another protein, the Leader (L), at the amino terminus of the viral polyprotein (FIG. 1A). The L protein is 67 aa long, with a novel CHCC zinc-finger motif, a highly acidic carboxyl domain (protein pI: 3.8), and no known homologs (FIG. 1). EMCV with L deletions are viable but have attenuated growth phenotypes (Dvorak, C. M. T., Hall, D. J., Hill, M, Riddle, M., Pranter, A., Dillman, J., Deibel, M. & Palmenberg, A. C. (2001) *Virology* 290, 261-271). They are inefficient at shutting off host protein synthesis (Zoll, J., Galama, J. M.D., van Kuppeveld, F. J. M. & Melchers, W. J. G. (1996) *J. Virol.* 70, 4948-4958), and they stimulate an increased antiviral IFN activity (Zoll, J., Melchers, W. J., Galama, J. M. & van Kuppeveld, F. J. (2002) *J. Virol.* 76, 9664-9672). For Theiler's murine encephalomyelitis virus the related L likewise affects nuclear trafficking. This slightly larger L (76 aa) stimulates IFN transcriptional activator IRF-3, normally a cytoplasmic entity, to redistribute aberrantly between the nucleus and cytoplasm. Simultaneously, polypyrimidine tract-binding protein, a nuclear component of prem-RNA splicing complexes, redistributes to the cytoplasm and is usurped into viral replication machinery. As a result, viral replication is enhanced by the cytoplasmic availability of polypyrimidine tract binding protein, and the cell is unable to mount a viable IFN-dependent antiviral response to the infection. The antitrafficking activities of EMCV and Theiler's murine encephalomyelitis virus are compromised if either virus harbors a mutation in the zinc-finger region of the L protein (Delhaye, S., van Pesch, V. & Michiels, T (2004) *J. Virol.* 78, 4357-4362). It has been proposed that the cardiovirus L, like the poliovirus/rhinovirus 2A$^{pro}$, disrupts the integrity of the NPC, leading to the leakage of nuclear proteins by passive diffusion (Lidsky, P. L., Hato, S., Bardina, M. V., Aminev, A. G., Palmenberg, A. C., Sheval, E. V., Polyakov, V. Y., van Kuppeveld, F. J. & Agol, V. (2006) *J. Virol.* 80, 2705-2717). However, it is difficult to envision how a small protein, lacking any known enzymatic activity, could effectively attack the massive NPC with the scant copy number presented to an infected cell.

In the work presented below, we hypothesized that an alternative target might be the nuclear transport system composed of Ran-GTPase or the cofactors required for maintaining the RanGTP gradient. We now describe experiments showing that the EMCV L binds directly to Ran and disrupts nucleocytoplasmic trafficking.

SUMMARY OF THE INVENTION

In one embodiment, the present invention is a method of inhibiting Ran protein activity in at least one eukaryotic cell or cell-free extract, the method comprising: exposing an amino acid sequence comprising at least a portion of purified EMCV or TMEV leader protein, wherein the amino acid sequence comprises SEQ ID NO: 14 or SEQ ID NO: 15, to at least one cell in an amount effective to inhibit Ran activity in the cell; and evaluating Ran protein activity in the cell or cell-free extract.

Preferably the amino acid sequence is a full-length EMCV leader protein. Most preferably, the sequence is SEQ. ID NOs: 1-8.

In another embodiment, the amino acid sequence is a full-length TMEV leader protein. Preferably, the sequence is SEQ. ID NOs: 9-13.

In another embodiment, the amino acid sequence is selected from modifications of SEQ. ID NOs: 1-13 wherein the acidic domain has been deleted.

In another embodiment, the amino acid sequences consist essentially of SEQ. ID NO: 14 or 15.

In another embodiment, step (b) comprises measuring the change in localization of cellular transport-specific proteins or RNA or step (b) comprises evaluating Ran inhibiting by measuring the ability of a cell-free extract to undergo Ran-dependent tubulin condensation into visible cellular spindle assemblies.

In another embodiment, the invention is a method of inhibiting Ran protein activity in a eukaryotic cell, the method comprising administering to a patient in need thereof a therapeutically effective amount of an amino acid sequence comprising at least a portion of EMCV or TMEV leader protein, wherein the sequence comprises SEQ. ID NO: 14 or SEQ. ID NO: 15, and determining the effect of inhibiting Ran activity in the patient.

Other features, objects and embodiments of the present invention will be apparent to one of skill in the art after review of the claims, specification, and drawings.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 6. Protein alignment of the Leader sequences of known cardioviruses. Dots ( . . . ) denote indels in relative sequence positions. Blue denotes virus strains in the TMEV species (Theiler's murine encephalomyelitis virus). All other strains belong to the EMCV species (encephalymyocarditis virus). Strain "emcv-r" was the experimental vector for experiments described below. The bold sequence is the 38 amino acid protein fragment expressed in LΔa. The red sequence is the minimum fragment within this deleted protein needed for inhibitory activity against Ran GTPase in cells or cell-free extracts. Note the strong conservation of this sequence among all EMCV. Sequence changes relative to emc-r are indicated in lower case. All TMEV are of similar sequence in this region, but all have natural deletions of 7 amino acids (relative to EMCV) near the amino terminus. These 7 amino acids are not required for Leader inhibition of Ran GTPase.

DESCRIPTION OF THE INVENTION

In General

The present invention provides methods of inhibiting Ran protein activity in eukaryotic cells by administering at least a portion of encephalomyocarditis virus (EMCV) leader protein to a cell, cell-free extract or to a patient in need. Ran protein activity is essential for metabolic processes including, but not limited to, nuclear transport, mitotic spindle assembly and cellular translation. The EMCV leader protein of the present invention provides a specific inhibitor of Ran activity, allowing these metabolic processes to be manipulated for therapeutic, preventative, research and diagnostic purposes.

Ran functions as a gatekeeper for nuclear pores, regulating, among other things, the interactions between nuclear transporter molecules and their cargo of proteins or nucleic acids that need to move into and/or out of a cell's nucleus. In use, Ran binds to guanosine triphosphate (GTP) within a cell's nucleus to provide one active form of the protein. In a cell's cytoplasm, Ran hydrolyzes the GTP to guanosine diphosphate (GDP) to form a different active form of protein. The resulting gradient of Ran-GTP and Ran-GDP across the nuclear envelope drives nuclear transport. By inhibiting Ran-GTP hydrolysis, or inhibiting Ran exchange of GTP for GDP, nuclear transport may be stopped or manipulated for therapeutic effect.

While Ran protein activity is fairly well understood, specific inhibitors of Ran protein activity are not. For instance, some picomaviruses, including EMCV, are known to inhibit nuclear transport (Delhaye et al, *J. Virology*, April 2004, 4357-4362). However, until now, the exact mechanism of inhibition has not been understood. The present application discloses how the EMCV leader protein binds to the Ran protein, thus inhibiting Ran activity in eukaryotic cells.

Suitable Leader Sequences

Figure 1:
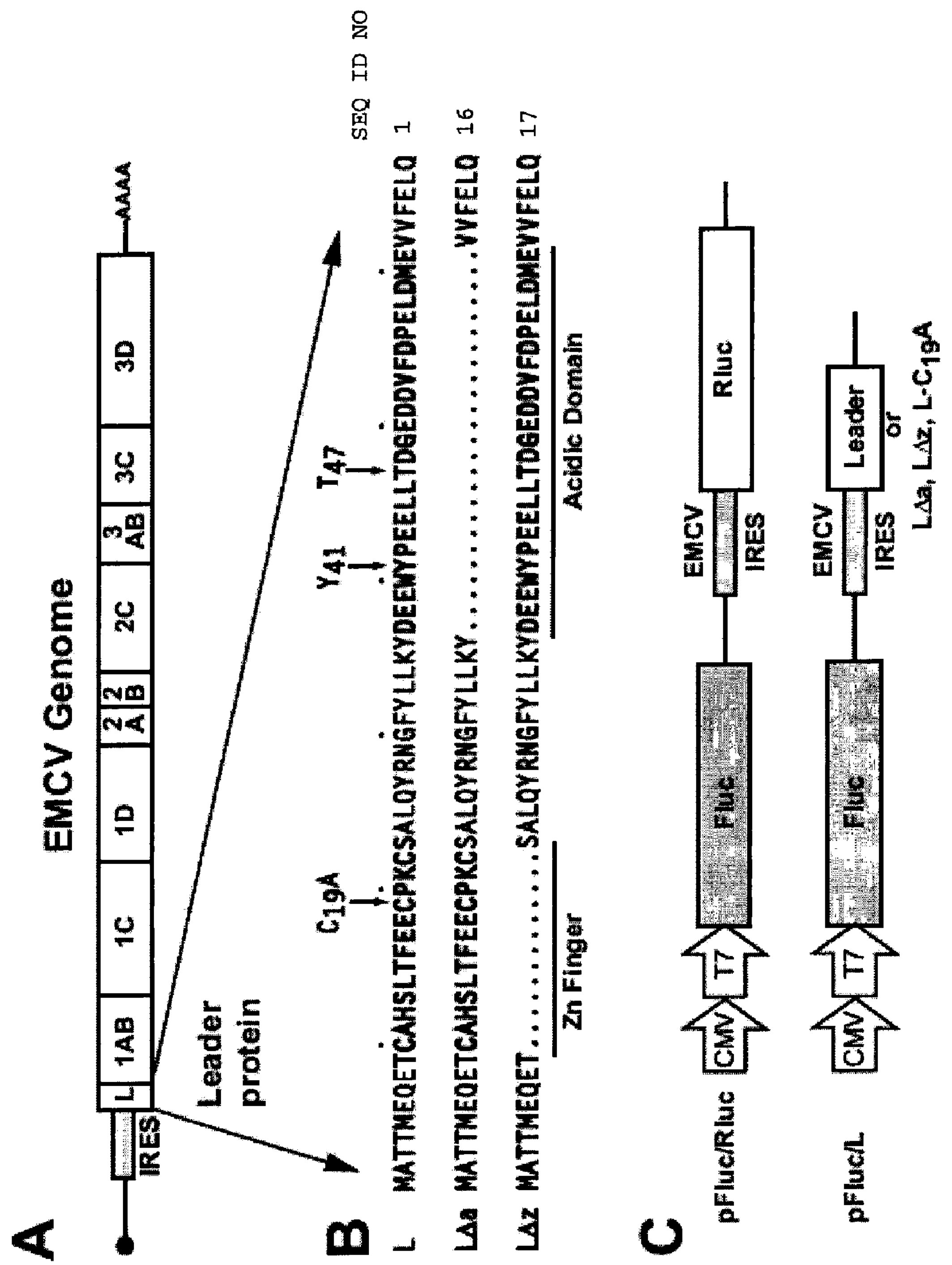
FIG. 1. Virus, Leader, and plasmid maps. (A) A genome map shows that EMCV L is derived from the amino terminus of the polyprotein. (B) The L, L(Δa), and L(Δz) sequences highlight the zinc-finger motif (amino acids 10-23) and acidic domain (amino acids 37-61). (C) Bicistronic cDNAs drive Fluc expression from a capped mRNA and the coexpression Rluc or the L proteins from an internal EMCV IRES.

The methods of the present invention require an L protein or segment of an L protein capable of inhibiting Ran activity. Viruses of the EMCV species of the Cardiovirus genus have a relatively short leader protein (L protein) comprising sixty-seven amino acids (Palmenberg et al., *Nucleic Acids Res.,* 1984, 12, 2969-2985, see FIGS. 1 and 6.) The EMCV leader protein shares only about 50% aligned amino acid identity with leader proteins of other related species of Cardioviruses (Dvorak et al., *Virology,* 2001, 290, 261-271). At this time, the EMCV leader protein has no known homolog or analog outside of this genus.

One version of the present invention provides a method of inhibiting Ran protein activity in a eukaryotic cell or cell-free extract comprising (1) administering to the cells or cell-free extract an effective amount of at least a portion of the EMCV leader protein, thereby inhibiting Ran activity in the cells, and (2) determining the effect of inhibiting Ran activity in the cells. In one preferred version, the EMCV leader protein comprises the complete sequence of sixty-seven amino acids (Palmenberg et al., *Nucleic Acids Res.,* 1984, 12, 2969-2985). FIG. 6 lists the entire L protein sequence from all known EMCV strains. All of these sequences, or any sequence from any other EMCV strain, are suitable for the present invention. Note that all of the EMCV L protein sequences are SEQ. ID NOs: 1-8.

FIG. 6 also lists the amino acid sequences of the L protein of Theiler's murine encephalomyelitis virus (TMEV). Both EMCV and TMEV are cardioviruses. The L protein from TMEV would be suitable for the present invention. Therefore, one may wish to use SEQ. ID NOs 9-13 in the present invention.

However, the EMCV or TMEV leader protein is therapeutically effective in smaller sizes. For instance, Applicants have shown that some internal deletions or external truncations are still effective Ran inhibitors. External truncations (ranging from one to nine amino acids from either the C terminal or N terminal of SEQ. ID NOs: 1-13) may be removed from the terminal ends of the protein. In an especially preferred embodiment of the invention, one may remove between 1 and 5 amino acids from either end of the EMCV or TMEV amino sequences of FIG. 6.

Internal deletions (ranging from 1-25 amino acids) preferably remove the acidic domain (amino acids 37-61 in SEQ. ID NO: 1). In one preferred embodiment, the amino acid sequence consists of an EMCV or TMEV leader protein sequence with a deletion of the entire acidic domain. In one preferred alternate version, the amino acid sequence consists of a 38 amino acid sequence (residues 1-32 and 75-80 in emc-r in FIG. 6) totally eliminating the acidic domain residues 34-74 in emc-r sequence (SEQ. ID NO: 1). Results have shown this sequence to be an equally effective inhibitor as the complete EMCV leader protein. Residues 1-2 linked to 9-27 of SEQ. ID NO: 1 are the minimum necessary sequence. The minimum amino acid fragment within the deleted protein that has been found to be necessary for Ran inhibition is SEQ. ID NO: 14 (derived from EMCV) and SEQ. ID NO: 15 (derived from TMEV). SEQ. ID NOs: 14 and 15 consist of the following residues:

tional amino acids can be added to either end of the amino acid sequence and not change the biological function. Most preferably, these amino acids are naturally occurring EMCV or TMCV amino acids. This would include EMCV or TMEV amino acids that have been excised from within the consensus core sequences.

In a further version, the present invention provides a composition comprising a therapeutically effective amount of the EMCV or TMEV leader protein and a pharmaceutically acceptable carrier or biologically inert fusion protein. In another embodiment of the present invention, the composition comprises a therapeutically effective amount of a fragment of the EMCV or TMEV leader protein wherein the fragment comprises the minimum necessary sequence, SEQ. ID NO: 14 or SEQ. ID NO: 15. By "pharmaceutically acceptable carrier" we mean to include carriers suitable for application to a patient or to eukaryotic cells or cell culture.

The present invention preferably employs a "purified" L protein. By "purified" we mean the L protein content is enriched relative to other EMCV and TMEV proteins. Therefore, by "purified", preferably we mean recombinant L produced from cDNAs which encode only the L gene in the absence of the rest of the viral genome (e.g. made in bacteria, baculovirus, etc).

Method of the Present Invention

In another embodiment, the present invention provides a method of inhibiting Ran protein activity in one or more specific eukaryotic cells or cell free in-vitro systems. The method comprises exposing at least a portion of the EMCV or TMEV Leader protein to the cell(s) in an amount effective to inhibit Ran activity within the targeted cell(s) or cell-free systems and determining the effect of inhibiting Ran activity in the targeted cell(s) or cell-free system. As described above, in a preferred version, the entire EMCV or TMEV leader protein sequence is used. However, certain smaller fragments of the EMCV or TMEV leader protein are effective (as described above). The Leader protein could be delivered either as a purified protein, or as expressed in cells or cell-free extracts, from a cDNA encoding the viral gene.

Preferably, the method of the present invention is as follows: purified recombinant L protein free of other cardioviral proteins would be delivered directly into permeabilized cultured cells or cell-free systems in an amount effective to inhibit Ran activity. The source of L could be purified protein, virus-infected cell extracts, or cell-free extracts containing L, generated through recombinant DNA technology.

L protein (or protein-containing extracts) would be added directly to permeabilized target cells which contained transport-active nuclei dependent on Ran activity. A minimum incubation time of 5 minutes is recommended at a preferable concentration of L, typically between 50 and 5000 nanomolar.

One would then evaluate the inhibitory effect of L on nucleocytoplasmic transport in cells, preferably by measur-

SEQ. ID NO: 14:
M■A■I/T■C■A/V■H■S■L/M■T■F■E/K■E/G■C■P■K■C■S■A■L■Q■Y;

SEQ. ID NO: 15:
M■A■C■I/K■H■G■Y■P■D/S■V■C■P■I■C■T■A■I/V■D■A/V/K.

In one embodiment of the present invention, the cell or cell-free extract is exposed to an amino acid sequence consisting essentially of SEQ. ID NOs: 14 or 15. By "consist essentially of," Applicants mean that one, two, or three addiing the change in localization (nuclear vs cytoplasmic) of cellular transport-specific proteins and RNA. In cell-free target systems without nuclei, one would add purified L (or cell extracts containing L) as described above, then evaluate Ran inhibition by measuring the ability of the extracts to undergo Ran-dependent tubulin condensation into visible cellular spindle assemblies.

In another embodiment of the invention, targeted eukaryotic cell(s) could be treated with L-encoding sequences, or injected, purified protein, to inhibit Ran activity. A number of delivery methods may be used, including protein microinjection or expression of the protein within the target cell by use of a recombinant DNA generated expression plasmids or gene-delivery vectors. In the preferred method, the L-encoding cDNA is delivered into target cells by transfection, using a plasmid encoding the L protein, or any other cDNA delivery method. Following delivery into the cell, cDNA is transported to the cell's nucleus by natural processes, transcribed into mRNA by cellular enzymes, then expressed into protein within the target cell. The expressed L protein is toxic to the Ran within that cell. A reduction in nucleocytoplasmic trafficking is observed as soon as the expressed L protein comes into contact with Ran, usually at times as early as 5 hours after introduction of the cDNA L toxicity (cell rounding and death) is commonly observed in all treated cells by 24 hours.

In an alternative application, the present invention provides a method of inhibiting Ran in a patient. This method comprises exposing at least a portion of the cardiovirus Leader protein to a patient, preferably a human patient, in an amount effective to inhibit Ran activity within targeted cells and thereby inhibiting nucleocytoplasmic trafficking. Potential cell targets include cancerous and other diseased tissues and other targets that would benefit from inhibited nucleocytoplasmic trafficking. Leader protein could be delivered to these tissues using viral gene therapy vectors or other technologies that would specifically deliver L-encoding genes to the targeted cell populations.

Of course, the description set out above is merely of exemplary preferred versions of the invention, and it is contemplated that numerous additions and modifications can be made. Note that further exemplary preferred versions of the invention are described in the appended pages, which are incorporated by reference an constitute a portion of this application. Specifically, Examples 1 and 2 provide examples and embodiments of the present invention.

EXAMPLES

Example 1

Figure 2:
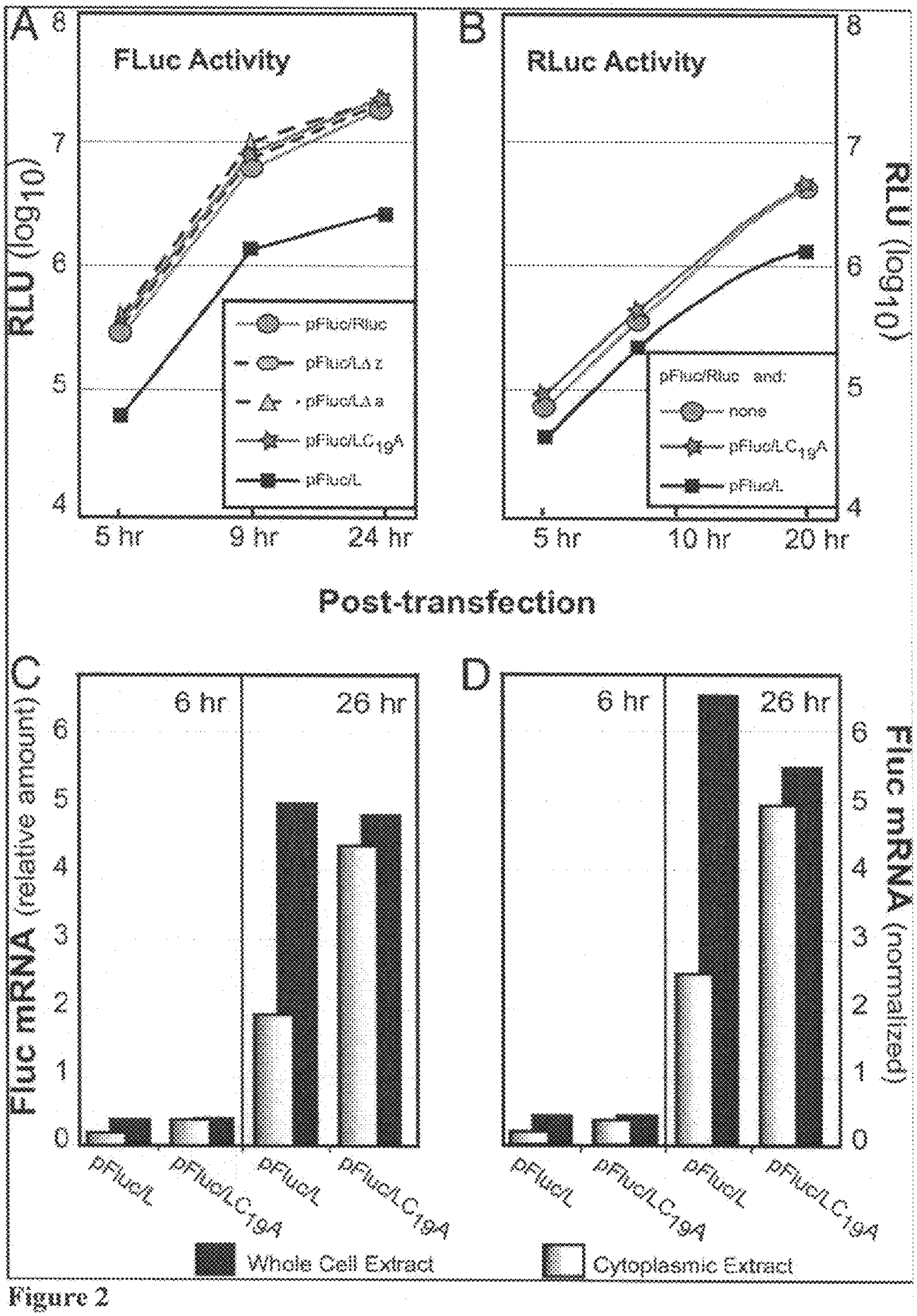
FIG. 2. Luciferase expression in the presence of Leader. (A) Plasmid cDNAs were transfected into HeLa cells, and Fluc activity [relative light units (RLU)] was assayed at the indicated times. Values are averages for duplicate samples (<10 RLU variance). (B) Plasmid pFluc/Rluc (1 μg per plate) was augmented with pFluc/L (1 μg per plate) or pFluc/L($C_{19}A$) (1 μg per plate) and then cotransfected into HeLa cells. Rluc activity (RLU) was assayed at the indicated times. The values are averages for duplicate samples (<10 RLU variance). (C)RNA from transfected cells prepared as in A were isolated from whole cells or cytoplasmic extracts. The relative Fluc RNA titers were assessed by quantitative PCR by using a standard curve derived for this sequence. (D) The β-actin mRNA titers were determined in parallel to C. The Fluc titers (from C) were normalized to the β-actin mRNA content observed at 6 h or 26 h in the pFluc/L($C_{19}A$) noninhibitory samples. This plot controls for changes in mRNA content from 6 to 26 h due to cell growth rather than transcription.

A Picornavirus Protein Interacts with Ran-GTPase and Disrupts Nucleocytoplasmic Transport Results L Alone Is Active Infection of cells with EMCV blocks active nucleocytoplasmic transport. Mutant viruses with L deletions do not effect the same response (Lidsky, P. L., Hato, S., Bardina, M. V., Aminev, A. G., Palmenberg, A. C., Sheval, E. V., Polyakov, V. Y., van Kuppeveld, F. J. & Agol, V. (2006) *J. Virol.* 80, 2705-2717.). Given the potential for synergy with other viral proteins, it has never been clear whether L alone was sufficient for this activity. We reasoned that if L were responsible for virus-induced shutoff, its activity should be maintained as an independent protein. Bicistronic cDNAs encoding EMCV L derivatives and *Renilla* luciferase (Rluc) or firefly luciferase (Fluc) reporter combinations were created to test this idea. Upon transfection, the cDNAs enter the nucleus and are transcribed from an internal CMV promoter. RNA transcripts are exported back to the cytoplasm, where translation of the 5' cistron is cap-dependent. Translation of the 3' cistron is driven by a native EMCV internal ribosome entry site (IRES). Compared to a control cDNA (pFluc/Rluc), Fluc activity from the 5' cistron was reduced 5- to 8-fold when L was expressed from the 3' cistron (pFluc/L) (FIG. 2A). Truncated L constructs, missing the zinc-finger domain (Δz) or the acidic domain (Δa), or with a point mutation ($C_{19}A$) that prevented zinc binding, were not inhibitory. L effects on 3' cistron expression were measured after simultaneous addition of different effector and reporter cDNAs (FIG. 2B). In this case, with a transfection efficiency of 60-80%, the IRES-driven Rluc activity (pFluc/Rluc) was diminished 3- to 6-fold whenever pFluc/L, but not pFluc/L($C_{19}A$), was included in the mix. The results show that L alone, in the absence of other viral proteins, was a potent down-regulator of new protein synthesis from both cistrons.

Because cell-free translation systems are not inhibited by the presence of L (Dvorak, C. M. T., Hall, D. J., Hill, M., Riddle, M., Pranter, A., Dillman, J., Deibel, M & Palmenberg, A. C. (2001) *Virology* 290, 261-271; Duke, G. M., Hoffman, M. A. & Palmenberg, A. C. (1992). *J. Virol.* 66, 1602-1609.), it is unlikely the measured inhibition was due to a cytoplasmic activity common to both IRES and cap-dependent translation. Rather, the results suggest that L affected some step in the mutual pathway used by all mRNAs, namely, a process inherent to nuclear mRNA synthesis, maturation, or export.

To test this hypothesis, the distribution of Fluc and β-actin mRNAs was measured in extracts derived from whole cells or fractionated cytoplasm after transfection with pFluc/L or pFluc/L($C_{19}A$) cDNAs. Appropriate sample preparation ensured that all signals were reverse transcriptase-dependent. Whether the Fluc mRNA signals were plotted relative to each other (FIG. 2C) or normalized to the β-actin content (FIG. 2D), the mutant and wild-type cDNAs each synthesized similar total levels of transcripts, which increased equivalently from 6 to 26 h. Therefore, L was not a direct inhibitor of mRNA transcription. Instead, when the total levels were compared to the cytoplasmic levels, it was obvious that L had an effect on mRNA distribution. In samples directed by pFluc/L($C_{19}A$), >91% of the whole cell signal was represented by the cytoplasmic signal, as expected for cells undergoing normal transcription and mRNA export. But for pFluc/L, less than half of the total signal was cytoplasmic at either time point. The remainder was in the nucleus, implicating L in a direct inhibition of mRNA export. Therefore, the decrease in Fluc/Rluc enzyme activities (FIGS. 2A and B) can be explained in part as a direct consequence of the smaller pools of cytoplasmic mRNAs available for translation. To be sure, an L-dependent down-regulation of its own mRNA export and expression, over the length of these assays, had the potential to trigger additional cell responses detrimental to Fluc/Rluc translation, including, e.g., PKR phosphorylation of initiation factor eIF2b (Sen, G. C. & Ransohoff, R. M. (1993) *Adv. Virus Res.* 42, 57-101.) or the nuclear sequestration (or turnover) of polypyrimidine tract-binding protein, poly(A) binding protein, or other ribosome factors. It will require a careful kinetic study with measured gene doses to parse such the translational responsibilities along the feedback loop of bicistronic expression, but, certainly, mRNA export was among the key pathways impinged by L, and L alone.

L Binds Ran-GTPase The EMCV L has no known enzymatic function, and its sequence lacks recognizable catalytic motifs. Reasonably, it must bind or sequester some component(s) essential to trafficking. The residue compositions of the zinc-finger and acidic domains evoke a weak comparison to the binding regions of RanGAP and RanBP1, respectively, that interact with Ran-GTPase (Seewald, M. J, Kraemer, A., Farkasovky, M., Korner, C., Wittinghofer, A. & Vetter, I. R.

Figure 3:
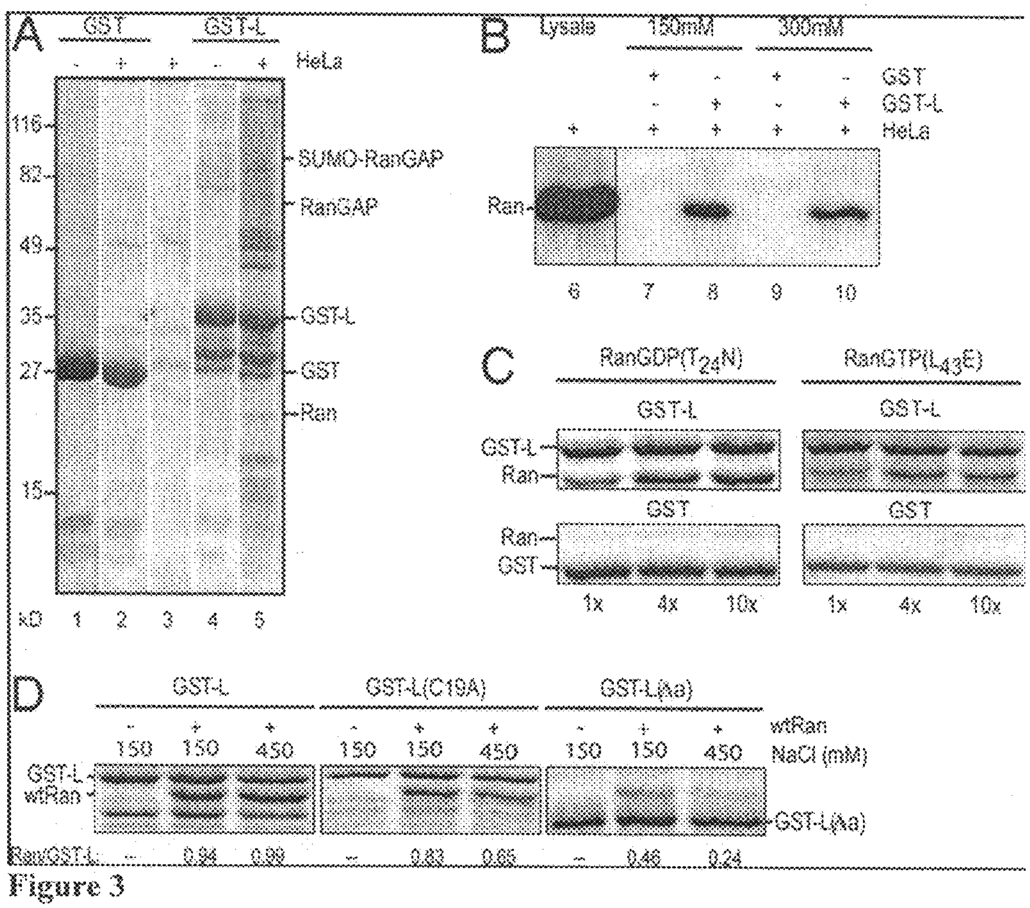
FIG. 3. Leader-Ran interactions. (A) Recombinant GST or GST-L, bound to glutathione beads, was reacted with HeLa extracts (lanes 2 and 5) or with buffer (lanes 1 and 4). Bound protein was fractionated by SDS/PAGE and then visualized after staining. Control beads without recombinant proteins were treated in parallel (lane 3). (B) GST or GST-L beads were incubated with HeLa extracts as in A. Before boiling, the beads were washed with 150 mM NaCl (lanes 7 and 8) or 300 mM NaCl (lanes 9 and 10). After SDS/PAGE, the bands were visualized by Western assay by using anti-Ran polyclonal antibodies. Unfractionated cell extract (lane 6) was included as a Ran marker. (C) GST or GST-L beads were incubated with the indicated molar equivalents of recombinant Ran ($T_{24}N$) or Ran($L_{43}E$). Extracted protein was fractionated by SDS/PAGE and then visualized by staining. (D) GST-L, GST-L($C_{19}A$), or GST-L(Δa) beads were incubated with (wild-type) Ran (1:4) as in C. The beads were washed with 150 mM or 450 mM NaCl as in B before the bound proteins were extracted, fractionated by SDS PAGE, and visualized by staining. Relative band intensities were captured (ImageQuant) and are presented as the ratio of Ran GST-L (or its derivatives) on the gels.

(2003) *Mol. Cell. Biol.* 23, 8124-8136.). We speculated that if L bound to Ran or its associated factors, active transport of mRNA or protein through the NPC might be inhibited. To explore this idea, recombinant L fused to GST was prepared. When bound to glutathione beads and incubated with cell lysates, GST-L, but not GST alone, extracted several bands of cellular proteins that could be visualized by staining (FIG. 3A). One of these bands was identified as Ran by immunoreactivity (FIG. 3B). The binding contacts between GST-L: Ran, or with the complex that contained Ran, were strong enough to resist disruption by 300 mM salt (FIG. 3B).

RanBP1 and RCC1 are not present, but Western assays (data not shown) have detected RanGAP and SUMO-RanGAP, a modified derivative. Several additional bands are in reasonable agreement with NTF2, importin β, and Crm1, members of the large family of known Ran contact proteins (Macara, L G. (2001) *Microbiol Mol. Biol. Rev.* 65, 570-594.). The cohort of cellular proteins bound to any particular Ran is intrinsically dependent on the status of the current nucleotide (GTP, GDP, or "empty"). As Ran cycles within cells or extracts, these populations can fluctuate dramatically. Therefore, the exact contacts that initiate pull-down in such experiments are difficult to assign, because any of the Ran nucleotide formats has the potential to react differently with the beads, or with different forms of L, or through different auxiliary proteins.

To determine whether the L extraction of Ran had been direct or required mediation by other proteins, GST beads and GST-L beads were incubated with recombinant Ran($L_{43}$E) or Ran($T_{24}$N). These forms are nucleotide-independent structural mimics of RanGTP and RanGDP, respectively, and they do not undergo GDP/GTP exchange or hydrolysis (Lounsbury, K. M., Richards, O. C., Carey, K. L. & Macara, I. G. (1996) *J. Biol. Chem.* 271, 32834-32841.). When the retained complexes were visualized by staining, all samples showed (approximately) 1:1 molar ratios of GST-L:Ran, regardless of the input concentrations (FIG. 3C). The assay showed no apparent specificity for either Ran conformation. Both forms bound equivalently in a L-dependent manner, and neither bound to GST alone. Therefore, Ran itself is a binding partner for L, regardless of its nucleotide-dependent conformation. Furthermore, when the mutant L sequences were configured as recombinant proteins and tested in similar assays (FIG. 3D), neither GST-L($C_{19}$A) nor GST-L(Δa) bound as effectively to (wild-type) Ran. Beads with the mutant proteins retained 10-50% less Ran than GST-L at 150 mM salt, and the binding was further reduced (30-70%) at 450 mM salt. This weakened stability is consistent with an impaired L:Ran interaction in the observed mutant phenotypes.

Figure 4:
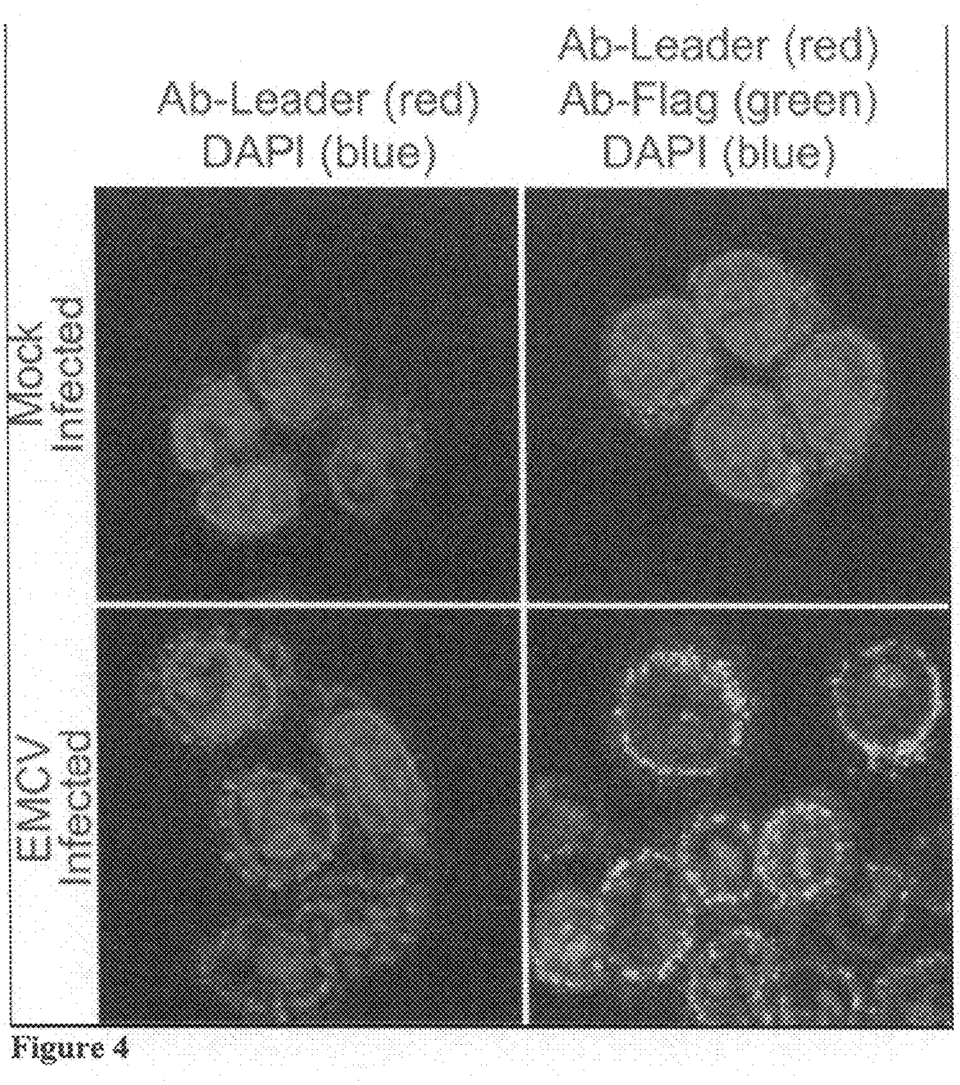
FIG. 4. Leader localization. HeLa cells were mock-infected or infected with vEC9-Flag. At 5 h after infection, the cells were fixed and stained with primary antibodies against L (polyclonal rat serum) or Flag (polyclonal mouse serum); DAP1 (blue) was included as a DNA marker. After reaction with appropriate secondary antibodies (red is anti-rat, and green is anti-mouse), image capture was as described in Example 1, Materials and Methods.

L Localizes Near the NE Ideally, in pull-down experiments there is reciprocity in reagents. It would be interesting to know, for example, whether recombinant Ran or its antibodies could extract L from infected cells. Unfortunately, our Ran antibodies are ineffective reagents for pull-down experiments even with uninfected cells, and, as an added complication, native L is very small and highly charged. In the absence of a tag like GST, L is not retained on membranes for Western assays. Furthermore, antibodies against recombinant L are only weakly reactive to the native protein. Still, when used to probe infected cells by confocal microscopy, these antibodies formed a pattern of dots, like a necklace of beads, around the outer regions of NE (FIG. 4). To better resolve this signal, a Flag tag was fused to the amino terminus of L in a recombinant virus context. After infection the Flag signal overlapped with that of L and augmented the necklace effect near the NE. Although preliminary, these localizations are at least indicative of a potential L locale near the cytoplasmic side of the NPC.

L Inhibits Ran-Dependent Mitotic Spindle Assembly During mitosis in normal cells the NPCs and NE are dismantled. A natural Ran gradient persists nonetheless because RanGTP can be generated locally by chromatin-bound RCC1, whereas RanGAP and RanBP1 ensure that the remainder is hydrolyzed to the GDP form throughout the cytoplasm (Kalab, P., Weis, K. & Heald, R. (2002) *Science* 295, 2452-2456; Caudron, M., Bunt, G., Bastiaens, P. & Karrmnti, E. (2005) *Science* 309, 1373-1376.). As a consequence, "cargo" remains inexorably bound to importin β everywhere except near the chromatin. Among the favored mitotic cargos of importin β are protein factors that initiate mitotic spindle assembly (Wiese, C., Wilde, A., Moore, M. S., Adam, S. A., Merdes, A. & Zheng, Y. (2001) *Science* 291, 653-656; Nachury, M, Maresca, T., Salmon, W., Waterman-Storer, C., Heald, R. & Weis, K. (2001) *Cell* 104, 95-106; Gruss, O., Carazo-Salas, R., Schatz, C., Guarguaglini, G., Kast, J., Wilm, M., Le Bot, N., Vernos, I., Karsenti, E. & Mattaj, I. (2001) *Cell* 104, 83-93). Consequently, spindles form preferentially near chromatin, where the RanGTP concentrations are high enough to dissociate these factors from importin β (Wilde, A., Lizarraga, S. B., Zhang, L., Wiese, C., Gliksman, N. R., Walczak, C. E & Zheng, Y. (2001) *Nat. Cell Biol.* 3, 221-227.). Cell-free extracts that allow RanGTP to sequester importin P are commonly used to examine Ran activities. For example, in *Xenopus* egg extracts, tubulin polymerization into asters and spindle structures requires an obligate prior conversion of endogenous RanGDP into RanGTP, as catalyzed by RCC1 associated with added sperm chromatin (Dasso, M. (2002) *Curr. Biol.* 12, 502-508).

Figure 5:
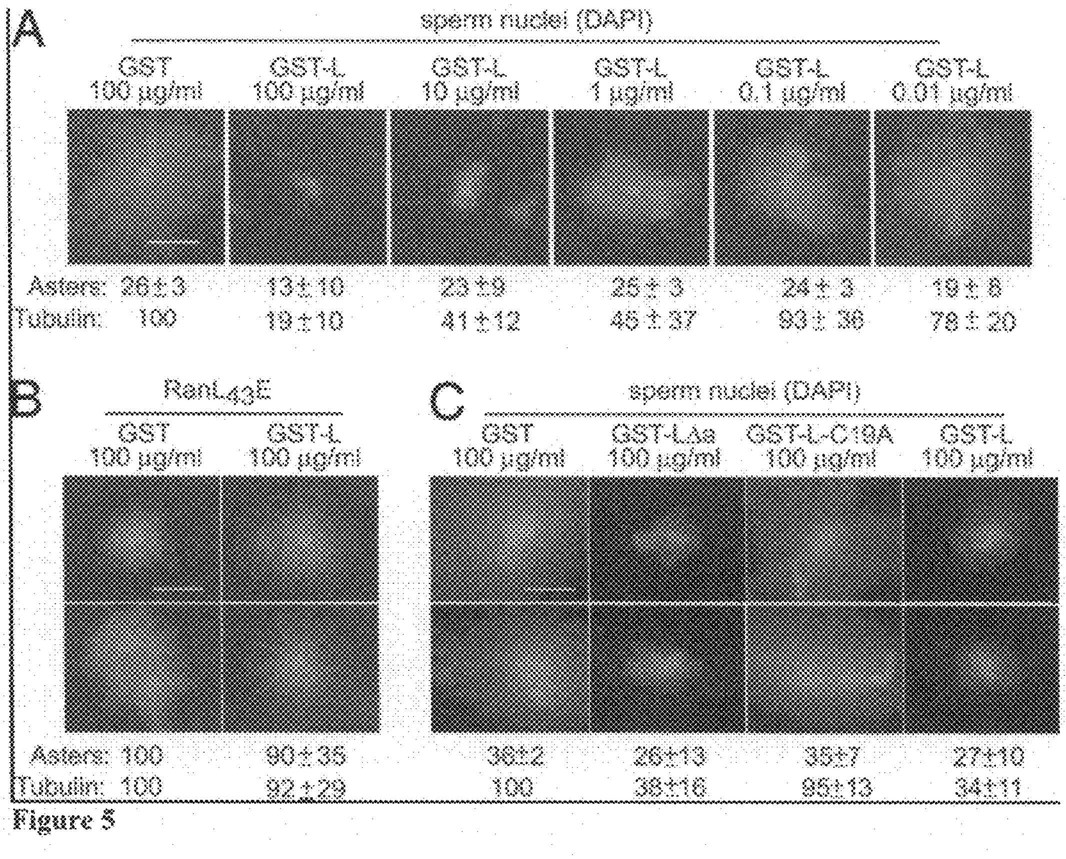
FIG. 5. Microtubule assembly assay. (A) *Xenopus* egg extracts were induced to form microtubule asters by the addition of sperm nuclei as described in Materials and Methods. The assays contained GST or GST-L at the indicated concentrations. Representative images were captured by fluorescence microscopy of rhodamine-labeled microtubules (red) or DNA (Hoechst dye, blue). In three separate experiments, the number of asters relative to GST alone was quantitated for 50 randomly selected microscope fields. Aster count and SD are indicated, along with the observed rhodamine florescence (tubulin) per aster (and SD) relative to the average intensity from control samples. (B) Assay conditions were similar to A except recombinant Ran($L_{43}E$) replaced sperm nuclei. The data are averages (and SD) from six independent experiments. (C) Assay conditions were identical to A, except GST-L(Δa) and GST-L($C_{19}$A) were tested in parallel to GST and GST-L. (Scale bars: 25 μm.)

Consistent with a role for L in the abrogation of Ran function, we found that recombinant GST-L, but not GST alone, was a potent inhibitor of sperm-induced aster formation (FIG. 5A). In repeated experiments, the addition of GST-L markedly reduced the number of observed asters relative to GST alone. The representative images also capture the dose-dependent reduction in rhodamine-labeled tubulin per aster, characteristically observed with GST-L. Typically, the count of chromatin units (blue) that generated asters was reduced by half, and the size of the asters that did form (red) was only 20% that of the controls.

To rule out nonspecific effects of L on this assay and determine whether the observed aster inhibition was indeed Ran-dependent, GST and GST-L were retested in a modified *Xenopus* egg system, where Ran($L_{43}$E), the RanGTP mimic, was added in place of sperm nuclei. Ran($L_{43}$E) can bind perpetually to importin β, circumventing the need for GTP hydrolysis or RCC1-facilitated nucleotide exchange. The asters that now formed in the presence of GST-L were indistinguishable in morphology and quantity from those of the control (FIG. 5B). Therefore, GST-L was not toxic to the generation of microtubule structures per se and did not interfere with the binding of Ran($L_{43}$E) to importin β. Rather, the presence of GST-L in the first experiment (FIG. 5A) must have prevented aster formation by inhibiting the generation of RanGTP.

Models for L Activity in Cells In contrast to cell-free assays, cellular forms of Ran are partitioned across the NE according to the activity and segregation of the Ran-associated factors. RCC1 is on chromatin. RanGAP and RanBP1 are predominantly cytoplasmic. Any activity that disrupts GDP/GTP exchange, or Ran cycling across the NE, has the potential to perturb the required cellular gradient and bring active trafficking to a halt. We do not yet know which specific step in the Ran pathway is impeded by L during EMCV infection. The combined data could be explained (i) if L prevented RanGTP hydrolysis or (ii) if L inhibited RanGDP/GTP exchange by RCC1. It is also possible that L works to accelerate RanGTP hydrolysis, because, in theory, a significant boost in GTPase activity could upset the endogenous gradient. But, given the rapidity with which L acts in cells during infection and the already high turnover of GTP during normal hydrolysis (Gorlich, D., Pante, N., Kutay, U., Aebi, U. & Bischoff, F. R. (1996) *EMBO J.* 15, 5584-55 94), we consider this model to be less probable. More logically, model i predicts that L binding to Ran might simply trap the GTP form on the cytoplasmic side of the NE, making it unavailable for further cycling. Indeed, this is where our antibodies localize L. Our mutants ($C_{19}A$ and Δa) with demonstrably lower binding affinities for Ran are doubtlessly defective because they are less efficient at this sequestration. Model ii predicts that L bound to RanGDP could become trapped in a cargo-bound form on the nuclear side of the membrane. In the absence of precise measurements of GDP/GTP exchange in cells and cell-free extracts, we cannot yet distinguish these scenarios. But either mechanism would presumably trigger the same effect in cells, namely, a potent disruption of the RanGDP/GTP gradient across the NE and a rapid, significant, probably irreversible block to active nucleocytoplasmic transport of protein (in) and cellular mRNA and protein (out). Either model might also explain other reported phenotypes currently attributed to L, including host protein synthesis inhibition and adverse IFN responses. Most likely, the L phenomenon is not IFN-specific but, rather, a general consequence of L-dependent destruction of the Ran gradient during infection.

Format of the Active L Many previous descriptions of L phenotypes have relied on L(Δa) and L(Δz) mutations to remove large portions of the protein (Dvorak, C. M. T., Hall, D. J., Hill, M., Riddle, M., Pranter, A., Dillman, J., Deibel, M. & Palmenberg, A. C. (2001) *Virology* 290, 261-271; Lidsky, P. L., Hato, S., Bardina, M. V., Aminev, A. G., Palmenberg, A. C., Sheval, E. V., Polyakov, V. Y., van Kuppeveld, F. J. & Agol, V. (2006) *J. Virol.* 80, 2705-2717). Other mutations have suggested that phosphorylation at Tyr-41 (Dvorak, C. M. T., Hall, D. J., Hill, M., Riddle, M., Pranter, A., Dillman, J., Deibel, M. & Palmenberg, A. C. (2001) *Virology* 290, 261-271) or Thr-47 (Zoll, J., Melchers, W. J., Galama, J. M. & van Kuppeveld, F. J. (2002) *J. Virol.* 76, 9664-9672) may influence functionality. Given the efficiency of the spindle assembly assays as a test for Ran activity, we prepared two additional recombinant variants of L and tested them for aster inhibition, carefully quantitating (×3)the number of asters per sperm (50 nuclei), and the relative tubulin content per aster (FIG. 5C). As before (FIG. 5A), GST-L showed a marked decrease (25%) in the number of asters per field and a reduction (66%) in the amount of tubulin per aster when compared with GST alone. The GST-L($C_{19}A$) was not inhibitory. It allowed about the same number of asters, with the same amount of tubulin, as the GST control. The results suggest that the zinc-finger motif within L is a key element for observation of Ran inhibition. Reinforcing this idea, the second recombinant protein, GST-L(Δa), was a strong inhibitor of aster formation. This fragment represents only a 42-a a piece of L. It lacks the acidic domain and both potential phosphorylation sites, yet its activity was equivalent to full-length L in this assay. This finding is of special interest, because the identical L(Δa) sequence expressed in cells from a bicistronic cDNA behaved like zinc-finger mutations L(Δz) and L($C_{19}A$) and was not inhibitory to Fluc expression (FIG. 2A). This finding suggests a special requirement for the acidic region in cells, but not in cell-free assays. Perhaps, as suggested by recombinant Ran-binding assays (FIG. 3D), the acidic domain and its potential phosphorylation sites are responsible for additional Ran impedance activities or increased binding affinities evident only in cells. Nevertheless, in cell-free extracts, we propose that this very limited fragment might be a very useful tool for further investigations into Ran functions during nuclear transport and mitotic spindle assembly. Recently, the NMR structure of the amino-terminal portion (32 residues) of the Mengoviral L was solved in a collaborative effort with the Center for Eukaryotic Structural Genomics (University of Wisconsin, Madison, Wis.). The coordinates (Protein Data Bank ID code 2BAI) show limited structural flexibility in the zinc-finger region, consistent with the idea that this unique domain could be involved as a primary Ran contact.

Materials and Methods

Bicistronic Plasmids. Bicistronic vector pFluc/—was a generous gift from R. Groppo (University of Wisconsin, Madison, Wis.). The plasmid has an immediate—early cytomegalovirus promoter ($P_{CMV}$IE) that drives transcription of capped, polyadenylated mRNA after transfection into cells. The 5' cistron (cap-dependent translation) of the mRNA encodes a full-length Fluc gene flanked on the 3 side by a wild-type EMCV IRES (Aminev, A. G., Amineva, S. P. & Palmenberg, A. C. (2003) *Virus Res.* 95, 45-57). In plasmid pFluc/Rluc, a full-length Rluc gene was linked to the start codon of the IRES. In plasmids pFluc/L, pFluc/L(Δz), and pFluc/L(Δa), the EMCV L, L(Δz), or L(Δa) sequences (Dvorak, C. M. T., Hall, D. J., Hill, M, Riddle, M, Pranter, A., Dillman, J., Deibel, M. & Palmenberg, A. C. (2001) *Virology* 290, 261-271) replaced the Rluc gene. For pFluc/L($C_{19}A$), two-step PCRs changed the wild-type Cys-19 to Ala (UGC to GGC) in the L gene. The identity of all cDNAs was confirmed by restriction analysis and sequencing. HeLa cell monolayers were transfected with plasmid DNAs by using liposomes (Rose, 7. K., Buonocore, L. & Whitt, M. A. (1991) *BioTechniques* 10, 520-525). Fluc and Rluc activities were assayed in cell lysates at appropriate times after transfection by using a dual luciferase assay system (Promega, Madison, Wis.) according to the manufacturer's instructions.

Quantitative PCR. Primersequences for the detection of Fluc and human β-act in mRNAs were designed by using Primer Express software (ABI, Foster City, Calif.). Total or cytoplasmic RNAs were isolated from transfected HeLa cells (duplicate plates) by using RNeasy mini kits (Qiagen). DNA contamination was reduced by treatment with RQ1 DNase (Promega) followed by an RNeasy step. The process was repeated a second time. Treated RNA (10 μl) was reacted (in 20 μl) with Moloney murine leukemia virus reverse transcriptase (M-MLV; Invitrogen, Carlsbad, Calif.) in the presence of appropriate primers (2 pg of primers flanking Fluc or β-actin). The cDNAs were diluted (10×) and then used to program duplicate (25 μl each), real-time PCR amplifications by using SYBR Green PCR master mix (ABI) and flanking primers as appropriate for each gene. The Fluc signal was normalized to the β-actin signal (Sequence Detection System software). Controls (2×) for each primer pair, in which water or an RNA sample without an RT-MLV step was replaced for template cDNA, were used in each experiment.

Recombinant L. The EMCV L segment from $pEC_9$ (Hahn, H. & Palmenberg, A C. (1995) *J. Virol.* 69, 2697-2699) was amplified by PCR and then ligated into pGEX-P2 (GE Bioscience, Piscataway, N.J.) to form plasmid pGST-L. Similar procedures linked the L(Δa) and L($C_{19}A$) segments into analogous plasmids. *Escherichia coli* (BL-21) was transformed with these plasmids, amplified, and induced with isopropyl β-D-thiogalactoside. Four hours later the cells were lysed, and the extracts were reacted with glutathione Sepharose HP resin (GE Bioscience). The bound proteins GST, GST-L, GST-L(Δa), and GST-L($C_{19}$A) were eluted (50 mM Tris, pH 8/10 mM reduced glutathione) and then analyzed for content and purity by SDS/PAGE.

For binding studies with cell extracts, confluent HeLa cell monolayers (6×106 cells) were washed with PBS and then lysed (0.5 ml of 50 mM Hepes, pH 7.4/150 mM NaCl/2 mM DTT/1 mM PMSF/0.5% vol/vol IPEGAL CA-630). After clarification, the extracts were added to glutathione Sepharose 4B-beads (GE Bioscience) prereacted with GST, GST-L, GST-L($C_{19}$A), or GST-L(Δa). Incubation was for 1 h at 22° C., and then the beads were washed twice with buffer (50 mM Hepes/0.5% vol/vol IPEGAL CA-630) containing NaCl (150 mM and 300 mM). Protein bound to the beads was eluted with SDS (boiling), fractionated by SDS/PAGE (12%), and then visualized by Western blot analysis using a primary antibody against Ran (goat polyclonal IgG, C-20; Santa Cruz Biotechnology, Santa Cruz, Calif.). For binding assays with recombinant Ran, the GST- or GST-L-bound Sepharose beads were reacted with Ran, RanGTP($L_{43}$E), or RanGDP ($T_{24}$N) (Wilde, A. & Zheng, Y. (1999) *Science* 284, 1359-1362) at molar ratios of 1:1,4:1, or 10:1 in phosphate buffer (20 mM, pH 7.6) for 1 h. The beads were washed with buffer containing NaCl (150 mM or 450 mM)before bound proteins were eluted with SDS (boiling), fractionated by SDS/PAGE, and then visualized by staining with Coomassie R-250.

Confocal Microscopy. Recombinant virus $vEC_9$ was modified to encode a Hag tag (DYKDDDK) at the start of the polyprotein (MA-DYKDDDK-MATT). HeLa monolayers were infected at a multiplicity of infection of 20 (Rueckert, R. R. & Pallansch, M. A (1981) *Methods Enzymol.* 78, 315-325). At 4 h after infection, the cells were washed, fixed, permeabilized, and then reacted with appropriate primary and secondary antibodies or DAPI stain, as described previously (Aminev, A. G., Amineva, S. P. & Palmenberg, A. C. (2003) *Virus Res.* 95, 45-57). The images were visualized by laser confocal microscope. For L protein detection, the primary antibody was anti-L polyclonal rat sera (5 11-2) precleared by incubation with HeLa cells. The secondary antibody was TRITC-conjugated rabbit, anti-rat IgG (T-4280; Sigma, St. Louis, Mo.). The Hag tag was detected with a murine monoclonal (F3165, Sigma). The secondary antibody was FITC conjugated goat anti-mouse IgG (F5387; Sigma).

Egg Extract Preparation and Aster Assembly. CSF-arrested *Xenopus* egg extracts and demembranated sperm chromatin were pre-pared as described (Murray, A. W (1991) *Methods Cell Biol.* 36, 581-605). Microtubule structures were assembled by adding 25 μM Ran($L_{43}$E) (Wilde, A. & Zheng, Y. (1999) *Science* 284, 1359-1362) or chromatin (150 sperm per microliter) to an egg extract supplemented with rhodamine-labeled tubulin (0.2 mg/ml) and incubating (at 22-25° C. for 15 mm) as described (O'Brien, L. L., Albee, A J., Liu, L., Tao, W., Dobrzyn, P., Lizarraga, S. B. & Wiese, C. (2005) *Mol. Biol. Cell* 16, 2836-2847). GST or GST-L was diluted in CSF-XB (10 mM K-Hepes, pH 7.6/100 mM KC1/2 mM $MgCl_2$/0.1 mM $CaCl_2$/50 mM sucrose/5 mM EGTA) and added to the extract at final concentrations of 0.01-100 μg/ml. For quantitation of tubulin fluorescence, the images were captured at the same camera setting for all samples. Tm ages were quantified by using MetaMorph software. Briefly, fluorescence intensity of each aster was measured, and then a background Value was subtracted by using an equal-sized area on the same image. At least 16 asters were measured per sample. For Ran($L_{43}$E)-induced structures, the number of asters in 50 randomly chosen microscope fields was recorded.

Example 2

Cardiovirus Leader Inhibits Ran-Dependent Cargo Delivery in Reconstituted *Xenopus*-HeLa Nuclear Import Assays Abbreviations: EMCV, encephalomyocarditis virus; GFP, green fluorescent protein; GST, glutathione S-transferase; L, Leader protein; NES, nuclear export signal; NSL, nuclear localization signal; NPC, nuclear pore complex; TMEV, Theiler's murine encephalomyocarditis virus; VSV, vesicular stomatitis virus.

Introduction

Nuclear pore complexes (NPC's) are massive 125 megadalton proteinaceous structures that enable the traffic of RNA and proteins between the sites of nucleic acid synthesis in the nucleus and protein expression in the cytoplasm by forming an aqueous channel linking these two cellular compartments (Reichelt, R., A. Holzenburg, E. L. Buhle, M. Jarnik, A. Engel, and U. Aebi. 1990. *Correlation between structure and mass distribution of the nuclear pore complex and of distinct pore complex components. J Cell Biol.* 110:883-94.). These structures are assembled from ~30 integral proteins called nucleoporins or Nups in multiple ring-like layers with 8-fold symmetry (Rout, M. P., J. D. Aitchison, A. Suprapto, K. Hjertaas, Y. Zhao, and B. T. Chait. 2000. *The yeast nuclear pore complex: composition, architecture, and transport mechanism J Cell Biol.* 148:635-52.). The directionality and specificity of movement into or out of the nucleus is dependent on discrete nuclear localization (NLS) or nuclear export signals (NES) on cargo proteins (or adaptor proteins such as in RNA export) (Fornerod, M., M. Ohno, M. Yoshida, and I. W. Mattaj. 1997. *Crm1 is an export receptor for lucine rich nuclear export signals. Cell* 90:1051-60; Kalderon, D., W. D. Richardson, A. F. Markham, and A. E. Smith. 1984. *Sequence requirements for nuclear localization of Simian Virus* 40 *large T antigen. Nature* 311:33-8). These signal sequences allow for regulated docking and release from soluble nuclear transport receptors that shuttle across the NPC through a series of transient interactions with nucleoporin FG domains (Rexach, M., and G. Blobel. 1995. *Protein import into nuclei: association and dissociation reactions involving transport substrate, transport factors and nucleoporins. Cell* 83:683-92, Shah, S., S. Tugendreich, and D. Forbes. 1998. *Major binding sites for the nuclear import receptor are the internal nucleoporin Nupl* 53 *and the adjacent nuclear filament protein Tpr. J. Cell Biology* 141:31-49). This energy-dependent process is driven by the small GTPase Ran which exists in two guanine nucleotide bound forms, GDP or GTP which predominate on the cytoplasmic and nuclear side of the pore, respectively (Adam, S. A., R. S. Marr, and L. Gerace. 1990. *Nuclear protein import in permeabilized mammalian cells requires soluble cytoplasmic factors. J. Cell Biology* 111:807-16; Gorlich, D., and U. Kutay. 1999. *Transport between the cell nucleus and the cytoplasm. Annu Rev Cell Dev. Biol.* 15:607-60). Transport receptors have a low affinity for RanGDP and bind tightly to the GTP form which mediates the movement of cargos from one side of the NPC to the other (Gorlich, D., N. Pante, U. Kutay, U. Aebi, and F. R. Bishoff 1996. *Identification of different roles for RanGDP and RanGTP in nuclear protein import. EMBO J.* 15:5584-94). Import receptors such as importin β bind cargo in cytoplasm and release their load in the nucleus by interacting with RanGTP (Izaurralde, E., U. Kutay, C. von Kobbe, I. W. Mattaj, and D. Gorlich 1997. *The asymmetric distribution of the constituents of the Ran system are essential for transport into and out of the nucleus. EMBO J.* 16:6535-47). The importin 13-RanGTP complex then shuttles back to the cytoplasm, recycling the receptor for another round of import. Conversely, export receptors like CRM1 form heterotrimeric complexes with their cargo and RanGTP in the nucleus which upon entering the cytoplasm are disassembled by the conversion of Ran to a GDP form (Fornerod, M., M. Ohno, M. Yoshida, and I. W. Mattaj. 1997. *Crm1 is an export receptor for lucine rich nuclear export signals. Cell* 90:1051-60). Ran completes the trip by binding to NTF2 in the cytoplasm which traffics it back into the nucleus (Ribbeck, K., G. Lipowsky, H. M. Kent, M. Stewart, and D. Gorlich. 1998. *NTF2 mediates nuclear import of Ran. EMBO J.* 17:6587-98). The Ran gradient across the nuclear envelope is maintained by associated cofactors that are specific to the nuclear and cytoplasmic compartments (Izaurralde, E., U. Kutay, C. von Kobbe, L W. Mattaj, and D. Gorlich. 1997. *The asymmetric distribution of the constituents of the Ran system are essential for transport into and out of the nucleus. EMBO J.* 16:6535-47). RanGAP and RanBP1/2 are localized at the cytoplasmic face of the nuclear pore where they bind Ran and convert it to a GDP form by increasing its intrinsically low hydrolysis rate up to 10,000 fold (Bischoff, F. R., C. Klebe, J. Kretschmer, A. Wittinghofer, and H. Ponstingl. 1994. *RanGAP1 induces GTPase activity of nuclear rasrelated Ran. Proc. Nat. Acad. Sci. USA* 91:2587-91; Bischoff, F. R., H. Krebber, E. Smirnova, W. H. Dong, and H. Ponstingl. 1995. *Coactivation of RanGTPase and inhibition of GTP dissociation by Ran GTP binding protein RanBP1. EMBO J.* 14:705-15). In the nucleus RanGTP predominates due to the activity of the nucleotide exchange factor, RCC1 and the high concentration of GTP(Bischoff, F. R., and H. Ponstingl. 1991. *Catalysis of guanine nucleotide exchange on Ran by the mitotic regulator RCC1. Nature* 354:80-82. 6. Clarke, P. R., C. Klebe, A. Wittinghofer, and E. Karsenti. 1995. *Regulation of Cdc2/cyclin B activation by Ran, a Ras-related GTPase. J. Cell Sci.* 108:1217-25). In the absence of a Ran gradient nearly all active transport comes to a halt (Izaurralde, E., U. Kutay, C. von Kobbe, I. W Mattaj, and D. Gorlich. 1997. *The asymmetric distribution of the constituents of the Ran system are essential for transport into and out of the nucleus. EMBO J.* 16:6535-47). With the exception of a few Ran-independent pathways, such as those that mediate tRNA export and trafficking independently shuttling proteins, the only movement between the nucleus and the cytoplasm is the diffusion of molecules smaller than 40 KDa (Nakielny, S., and G. Dreyfuss. 1999. *Transport of proteins and RNA in and out of the nucleus. Cell* 99:677-90).

Many viruses are known to commandeer or abrogate nuclear transport processes for their own benefit (Gustin, K E. 2003. *Inhibition of nucleo-cytoplasmic trafficking by RNA viruses: targeting the nuclear pore complex. Virus Res.* 95:35-44). For cytoplasmically replicating RNA viruses, inhibition of active nucleocytoplasmic trafficking can block the transduction of antiviral signals to the nucleus and the export of RNA's that could be detrimental to viral replication or localize beneficial nuclear targeted proteins to the cytoplasm (Belov, G. A., P. V. Lidsky, 0. V. Mitkitas, D. Egger, K. A. Lukyanov, K. Bienz, and V. Agol. 2004. *Bidirectional increase in permeability of nuclear envelope upon poliovirus infection and accompanying alterations of nuclear pores. J. Virology* 78:10166-77; Gustin, K E. 2003. *Inhibition of nucleo-cytoplasmic trafficking by RNA viruses: targeting the nuclear pore complex. Virus Res.* 95:35-44). The RNA virus, vesicular stomatitis virus (VSV) encodes a matrix (M) protein that interferes with both export of spliced mRNAs, snRNAs, and snRNPs as well as import of proteins with common NLS signals by binding to a component of the nuclear pore complex (Her, L. S., E. Lund, and J. E. Dahlberg. 1997. *Inhibition of ran guanosine triphosphatase-dependent nuclear transport by the matrix protein of vesicular stomatitis virus. Science* 276:1 845-8; Petersen, J. M., L. S. Her, and J. E. Dahlberg. 2001. *Multiple vesiculoviral matrix proteins inhibit both nuclear export and import. Proc. Nat. Acad. Sci. USA* 98:8590-95; Petersen, J. M., L. S. Her, V. Varvel, E. Lund, and J. E. Dahlberg. 2000. *The matrix protein of vesicular stomatitis virus inhibits nucleocytoplasmic transport when it is in the nucleus and associated with nuclear pore complexes. Mol. Cell Biology* 20:8590-601). This interaction does not inhibit all trafficking pathways. The export of tRNAs was unaffected by M suggesting that it blocks a site critical for binding of specific import and export receptors. This activity is conserved among vesiculoviruses with similar inhibitory activity observed for the M protein of Chandalpura virus and spring viremia carp virus (Petersen, J. M., L. S. Her, and J. E. Dahlberg. 2001. *Multiple vesiculoviral matrix proteins inhibit both nuclear export and import. Proc. Nat. Acad. Sci. USA* 98:8590-95). A number of RNA picomaviruses also target the NPC in order to disrupt the normal movement of proteins and RNA between the cytoplasm and the nucleus. Nucleoporins p62 and Nup153 are degraded during poliovirus and rhinovirus infection which results in the inhibition of import pathways (Gustin, K. E., and P. Sarnow. 2001. *Effects of poliovirus infection on nucleo-cytoplasmic trafficking and nuclear pore complex composition. EMBO J.* 20:240-9, Gustin, K. E., and P. Sarnow. 2002. *Inhibition of nuclear import and alteration of nuclear pore complex composition by rhinovirus. J. Virology* 76:8787-96). However these changes do not appear to inhibit the function of CRM1/exportin 1, a primary export receptor for mRNA (Gustin, K. E., and P. Sarnow. 2001. *Effects of poliovirus infection on nucleo-cytoplasmic trafficking and nuclear pore complex composition. EMBO J.* 20:240-9). These cleavage events additionally appear to alter the exclusion limit of the NPC, inducing the efflux of a number of nuclear proteins into the cytoplasm (Belov, G. A., P. V. Lidsky, 0. V. Mitkitas, D. Egger, K. A. Lukyanov, K. Bienz, and V. Agol. 2004. *Bidirectional increase in permeability of nuclear envelope upon poliovirus infection and accompanying alterations of nuclear pores. J. Virology* 78:10166-77; Gustin, K. E., and P. Sarnow. 2001. *Effects of poliovirus infection on nucleo-cytoplasmic trafficking and nuclear pore complex composition. EMBO J.* 20:240-9; Gustin, K. E., and P. Sarnow. 2002. *Inhibition of nuclear import and alteration of nuclear pore complex composition by rhinovirus. J. Virology* 76:8787-96). The 2A protease encoded by these viruses is either directly or indirectly responsible for partially dismantling the NPC. Expression of poliovirus 2Apro alone in cells induces efflux of proteins from the nucleus comparable to viral infection (Belov, G. A., P. V. Lidsky, 0. V. Mitkitas, D. Egger, K. A. Lukyanov, K. Bienz, and V. Agol. 2004. *Bidirectional increase in permeability of nuclear envelope upon poliovirus infection and accompanying alterations of nuclear pores. J. Virology* 78:10166-77).

Changes in the distribution of nuclear targeted proteins are also observed during cardiovirus infection (Delhaye, S., V. van Pesch, and T Michiels. 2004. *The leader protein of Theiler's virus interferes with nucleocytoplasmic trafficking of cellular proteins. J. Virology* 78:4357-62, Lidsky, P. L., S. Hato, M. V. Bardina, A. G. Aminev, A. C. Palmenberg, E. V. Sheval, V. Y. Polyakov, F. J. van Kuppeveld, and V. Agol. 2006.

*Nucleo-cytoplasmic traffic disorder induced by cardioviruses. J. Virology* 80:2705-17). These more distantly related picomaviruses typified by encephalomyocarditics virus (EMCV) and Theiler's murine encephalomylelitis virus (TMEV) do not encode a homolog to 2A pro, instead they have a unique Leader (L) protein that has been identified as the etiologic agent of nuclear transport disruption (Lidsky, P. L., S. Hato, M. V. Bardina, A. G. Aminev, A. C. Palmenberg, E. V. Sheval, V. Y. Polyakov, F. J. van Kuppeveld, and V. Agol. 2006. *Nucleo-cytoplasmic traffic disorder induced by cardioviruses. J. Virology* 80:2705-17). L is an 8 kilodalton acidic protein (p1=3.8) that presents a pair of molecular binding motifs, a novel CHCC zinc-finger domain and an acidic domain. Since L lacks proteolytic activity it likely mediates these effects through direct interactions with cellular binding partners. Unlike for poliovirus and rhinovirus, p62 and Nup 53 are not degraded during cardiovirus infection also suggesting that L alters trafficking through a different mechanism (Lidsky, P. L., S. Hato, M. V. Bardina, A. G. Aminev, A. C. Palmenberg, E. V. Sheval, V. Y. Polyakov, F. J. van Kuppeveld, and V. Agol. 2006. *Nucleo-cytoplasmic traffic disorder induced by cardioviruses. J. Virology* 80:2705-17). We have previously shown that L binds directly to RanGTPase, the energy source for active import and export pathways (Porter, F. W., Y. Bochkov, A. J. Albee, C. Wiese, and A. C. Palmenberg. 2006. *A picornavirus protein disrupts nucleocytoplasmic transport by targeting Ran GTPase. Proc. Nat. Acad. Sci. USA* 103:12417-22). When added to in-vitro mitotic spindle assembly reactions, an assay for Ran cycling activity, L inhibited this process in a Ran-dependent manner. When expressed alone in cells, L also inhibited mRNA export suggesting that unlike 2Apro L also inhibited nuclear export pathways. However a direct link between the disruption of Ran cycling and nuclear import by L has not been established.

Here we employ a reconstituted nuclear import to assay to investigate the manner by which EMCV L protein disrupts nucleocytoplasmic trafficking. We demonstrate that recombinant L alone rapidly inhibited accumulation of cargo in HeLa nuclei in a Ran-dependent manner. This is evidenced by arrest of cargo at the nuclear periphery of NPCs in L treated samples and the restoration of import activity specifically by the addition of purified recombinant wild-type Ran. Additionally, the pre-exposure of nuclei to L did not inhibit import demonstrating that the NPC's are not permanently altered. Finally, we show that both the zinc-finger and acidic domain of recombinant L are important for its activity. Together these results support our hypothesis that L targets the soluble factor Ran to inhibit nucleocytoplasmic trafficking in EMCV infected cells and demonstrate the divergence in inhibitory mechanisms employed by different RNA picomaviruses to target this critical cellular process.

Materials and Methods

Recombinant Protein Expression and Purification: GST-GFP-NLS, a green-fluorescent nuclear import cargo encoding a wild-type SV40 large-T antigen nuclear localization signal was expressed in DH5α cells transformed with plasmid, pYZ4O5 (a kind gift of Christiane Wiese) following isopropyl β-D-thiogalactoside induction and purified from the resulting clarified cell extract using glutathione Sepharose HP resin (GE Biosciences, Piscataway, N.J.). The isolated protein was then dialyzed into 20 mM HEPES pH 7.3, 110 mM potassium acetate and analyzed for protein concentration and purity using Bio-Rad protein assay and SDS-PAGE, respectively.

His-tagged wild-type human Ran GTPase was expressed in BL21 cells from transformed with plasmid, pCW413 (a kind gift of Christiane Wiese) following isopropyl β-D-thiogalactoside induction and purified from the resulting clarified cell extract using HisTrap HP resin (GE Biosciences). The isolated protein was then dialyzed into 20 mM HEPES pH 7.3, 110 mM potassium chloride and analyzed for protein concentration and purity using Bio-Rad protein assay and SDS-PAGE, respectively.

GST, GST-L, and GST-L mutant fusion proteins were expressed and purified as described previously (Porter, F. W., Y. Bochkov, A. J. Albee, C. Wiese, and A. C. Palmenberg. 2006. *A picornavirus protein disrupts nucleocytoplasmic transport by targeting Ran GTPase. Proc. Nat. Acad. Sci. USA* 103:12417-22) and dialyzed into 20 mM HEPES pH 7.3, 110 mM potassium acetate.

*Xenopus* Egg Cytosol: Crude interphase *Xenopus* egg extracts were prepared as described earlier (Newmeyer, D. D., and K. L. Wilson. 1991. *Egg extracts for nuclear import and nuclear assembly reactions. Methods Cell Biol.* 36:607-34). Briefly, dejellied unactivated *Xenopus* eggs were crushed in 250 mM sucrose, 50 mM potassium chloride, 2.5 mM magnesium chloride, 1 mM dithiothreitol, 50 ug/ml cycloheximide, and 5 ug/ml cytochalasin B and frozen in liquid nitrogen. Thawed crude extracts were then thawed, centrifuged (16,100×g, 15 minutes, 4° C.), and the soluble fraction was snap frozen in single-use aliquots.

In-Vitro Nuclear Import Assay: Import reactions were performed here in a manner similar to previous reports (Adam, S. A., R. S. Marr, and L. Gerace. 1990. *Nuclear protein import in permeabilized mammalian cells requires soluble cytoplasmic factors. J. Cell Biology* 111:807-16). HeLa cells were grown as 60% confluent monolayers on 12 mm coverslips in 24 well dishes. Cells were washed once with ice-cold transport buffer (TB), (20 mM HEPES pH 7.3, 110 mM potassium acetate, 2 mM magnesium acetate, 1 mM EGTA, 2 mM dithiothreitol), permeabilized with 20 ig/ml digitonin, and washed again with TB.

Import mixtures (40 μl) containing TB, *Xenopus* egg cytosol, 1 mM ATP, 0.5 mM GTP, and 75 μg/ml GST-GFP-NLS were assembled on ice with or without added effector proteins (WGA (Sigma, L9640, Saint Louis, Mo.), GST, GST-L or GST-L mutants). Reactions were initiated by inverting coverslips on droplets of import mixture formed on Parafilm. Samples were then incubated in the dark for 35 minutes at 20° C. and stopped by diluting the import mixture 10-fold with ice-cold TB. Coverslips were washed twice with TB, fixed with 4% formaldehyde, and mounted on microscope slides using Vectashield mounting media (Vector Labs., Burlingame, Calif.).

Incubations with effector proteins before or after import were performed as described for the import reactions above without the addition of GST-GFP-NLS. Coverslips were then briefly washed with TB between the treatment and import reactions. Immunofluorescence NPC Localization Studies:

Following the formaldehyde fixing step described above, cells were washed once with TB and blocked with 10% newborn calf serum/1% BSA in TB for 1 hour. Nuclear pore complexes were visualized using MAb41 4 (MMS-1 20R, Covance, Berkeley, Calif.) and TRITC-conjugated goat anti-mouse IgG (T-5393, Sigma) as primary and secondary antibodies, respectively. DNA was visualized by adding 0.5 ig/ml DAPI stain during secondary antibody incubation.

Visualization and Quantitation of Import Results: Mounted samples were visualized with a Nikon Eclipse TE-2000U laser confocal microscope using a 60×/1.4 PlanApo objective. GFP, TRITC, and DAP1 signals were captured in series using 488, 543, and 405 nm wavelength lasers, respectively.

Fluorescence images were collected for all comparable samples using the identical microscope, laser and detector settings.

The amount of GST-GFP-NLS cargo in nuclei was quantitated by converting GFP-fluorescence images to greyscale in Adobe Photoshop C52 and analyzing the images using ImageQuant 5.2. In each image, the pixel density was determined for circles of identical dimensions within 10 representative nuclei. These values were averaged and the standard deviation was determined.

Line scans of GFP (cargo) and Mab41 4 signals were performed on grayscale images using ImageQuant 5.2. A 21 pixel wide line was used to quantitate signal intensity from each channel. Signals were de-noised by averaging the intensity of a 3 pixel window across the image.

GFP Immunoblotting: Samples of purified GST-GFP-NLS or import mixture were run on a 12% SDS PAGE gel and transferred to an Immobilon P membrane (Millipore, Mass.). The membrane was blocked with 10% nonfat dry milk in PBS-T and probed with anti-GFP rabbit polyclonal IgG (SC-8334, Santa Cruz-Biotech, Santa Cruz, Calif.). The protein was then detected with a horseradish peroxidase-conjugated goat anti-rabbit IgG secondary antibody (A0545, Sigma) and ECL detection reagent (GE Biosciences).

Results:

L blocks nuclear localization of fluorescent import cargo. Nucleocytoplasmic transport is blocked by EMCV infection and the expression of EMCV L alone in cells (Lidsky, P. L., S. Hato, M. V. Bardina, A. G. Aminev, A. C. Palmenberg, E. V. Sheval, V. Y. Polyakov, F. J. van Kuppeveld, and V. Agol. 2006. *Nucleo-cytoplasmic traffic disorder induced by cardioviruses. J. Virology* 80:2705-17; Porter, F. W., Y. Bochkov, A. J. Albee, C. Wiese, and A. C. Palmenberg. 2006. *A picornavirus protein disrupts nucleocytoplasmic transport by targeting Ran GTPase. Proc. Nat. Acad. Sci. USA* 103:1241 7-22). We have proposed that L induces this effect by disrupting the Ran gradient required for this essential cellular function. However, evidence to support this hypothesis is still lacking. To directly test the effect of L on nuclear import, we assembled an in-vitro assay using *Xenopus* egg cytosol as a source of essential soluble factors (eg, importins, Ran, NTF2) and digitonin treated HeLa cells as a source of nuclei. Import activity was assessed by the nuclear accumulation of a synthetic fluorescent cargo (GST-GFP-NLS) added to the reactions. This 55 kilodalton fusion protein with a SV40 T-antigen nuclear localization signal dimerizes under physiological conditions and cannot readily diffuse out of nuclei with intact NPCs following import (Mannervick, B., and U. H. Danielson. 1988. *Glutathione transferases structure and catalytic activity. CRC Crit. Rev. Biochem.* 23:283-337).

Figure 7:
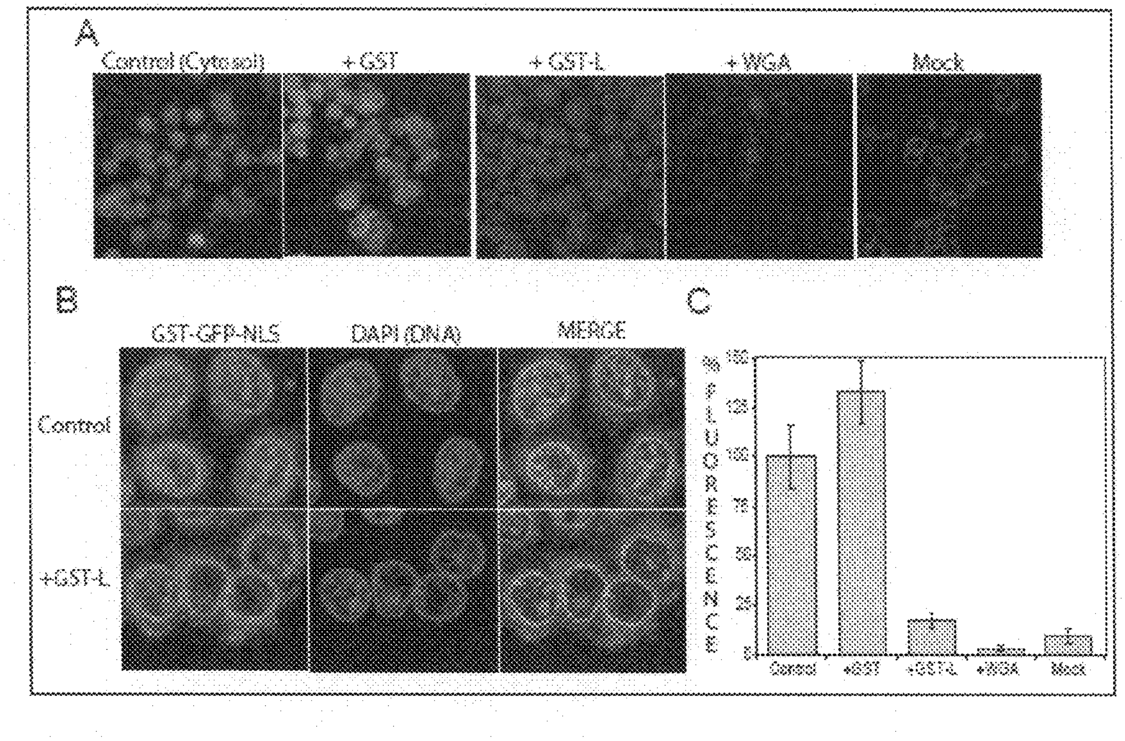
FIG. 7. Effect of L in reconstituted *Xenopus*-HeLa import reactions. Nuclear localization of the fluorescent import cargo, GST-GFP-NLS was measured following import as described in Example 2, Material and Methods. Import was performed in the presence of *Xenopus* cytosol alone (Control) or with added effector proteins (GST, GST-L, WGA). The concentrations of GST, GST-L, and WGA were 100 μg/ml, 105 μg/ml and 500 μg/ml, respectively. Mock reactions were performed in the absence of cytosol in TB buffer. (A) Confocal microscope images of GFP cargo distribution in nuclei following import with different treatments. (B) Localization of cargo in control and L treated samples was assessed by co-staining with DAP1 following import. (C) Percent nuclear cargo accumulation versus the control was determined from the average intensity of GFP fluorescence as described in Materials and Methods. The standard deviation for each sample is shown by the error bars.

We reasoned that if L inhibited nucleocytoplasmic trafficking in a Ran-dependent manner; it should have a significant effect when present during nuclear import. When we compared import activity of reactions containing *Xenopus* cytosol and purified recombinant GST-L to controls without added protein or with purified GST alone, we observed a dramatic difference in cargo distribution. Nuclei from the control reactions (cytosol, cytosol+GST) contained cargo throughout the interior while those treated with GST-L showed a faint fluorescence signal within nuclei and a ring-like pattern near the nuclear periphery (FIG. 7A). This pattern of cargo distribution differed from the phenotypes observed when import was inhibited by the absence of cytosol (mock), or the presence of wheat germ agglutinin (WGA), a lectin known to bind nucleoporins and block the movement of cargo through the pore (Finlay, D. R., D. D. Newmeyer, T. M. Price, and D. J. Forbes. 1987. *Inhibition of in-vitro nuclear transport by a lectin that binds to nuclear pores. J Cell Biol.* 104:189-200). In these samples, the cargo was primarily excluded from nuclei and detected at low levels in the cytoplasmic compartment. To examine whether the ring-like pattern of substrate induced by L was inside the nucleus, we labeled the samples with DAP1 stain following import. In control samples, the GFP fluorescence was observed throughout the nucleus while in those treated with L the signal was predominantly co-localized with the peripheral DAP1 stain, suggesting that the cargo was at the nuclear rim (FIG. 7 B).

Figure 8:
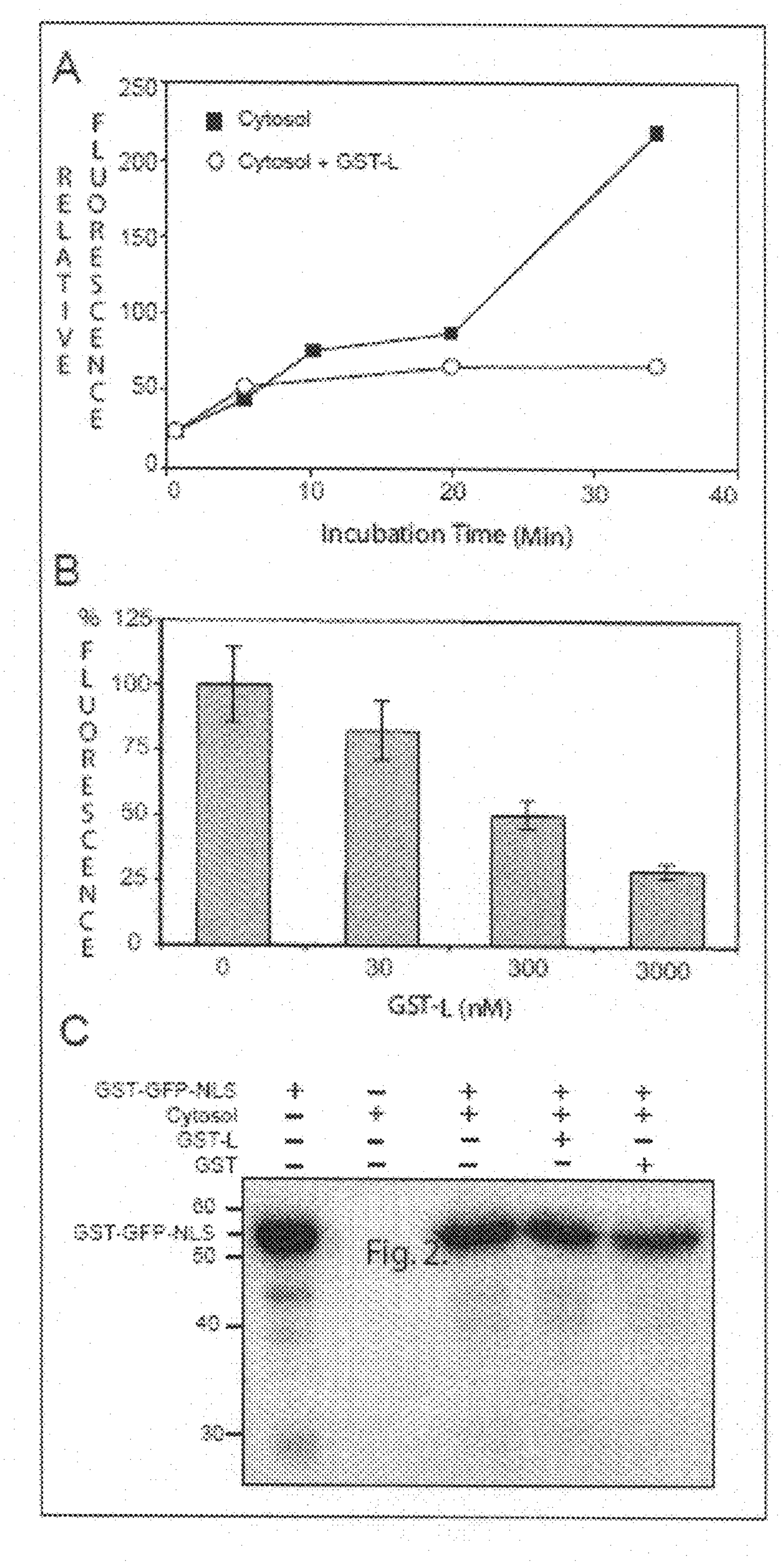
FIG. 8. Characteristics of L inhibition. (A) The kinetics of cargo accumulation in control and L treated nuclei was determined over a 35 minute timecourse. Average nuclear cargo accumulation was determined for each sample as described in Materials and Methods and was plotted on a relative scale. (B) The effect of GST-L concentration on nuclear cargo accumulation was determined over a 100-fold range at a 35 minute assay endpoint. Average cargo accumulation was determined for duplicate samples as in A. and plotted as percent of control. (C) The stability of GST-GFP-NLS was determined by anti-GFP immunoblot following incubation for 35 minutes in import reactions with or without added GST effector proteins as described in Materials and Methods. The first lane shows purified cargo protein at an identical dilution in TB buffer.

Using image analysis software we quantified the effects of each treatment. The intensity of nuclear GFP fluorescence was determined and averaged for 10 representative nuclei from each sample. The GST, GST-L, mock and WGA treatments resulted in nuclear fluorescence intensities of 133, 17, 10, and 3 percent of the control, respectively (FIG. 7 C). Since L may require time to dissipate a pre-existing RanGTP gradient, we predicted that the small amounts of cargo present in L treated nuclei were imported shortly after the start of the reaction. Time course studies revealed that import in control and L treated samples was comparable for the first 5 minutes of the assay but that incubation with L rapidly blocked additional cargo accumulation, consistent with this hypothesis (FIG. 8A). To determine the amount of L required to induce this effect we tested a range of concentrations for their inhibitory activity. These experiments showed that inhibition was most pronounced at low micromolar (3 μM) concentrations of L. Reducing the concentration 10 and 100-fold resulted in a 50%, and 90% reduction in its inhibition (FIG. 8B). To investigate the possibility that L induced degradation of the GST-GFP-NLS cargo, we performed a GFP-western blot on import samples at the assay endpoint. Comparable patterns were observed in Control, GST-L, and GST containing samples suggesting that the effect of L was not due to cargo proteolysis (FIG. 8C).

Figure 9:
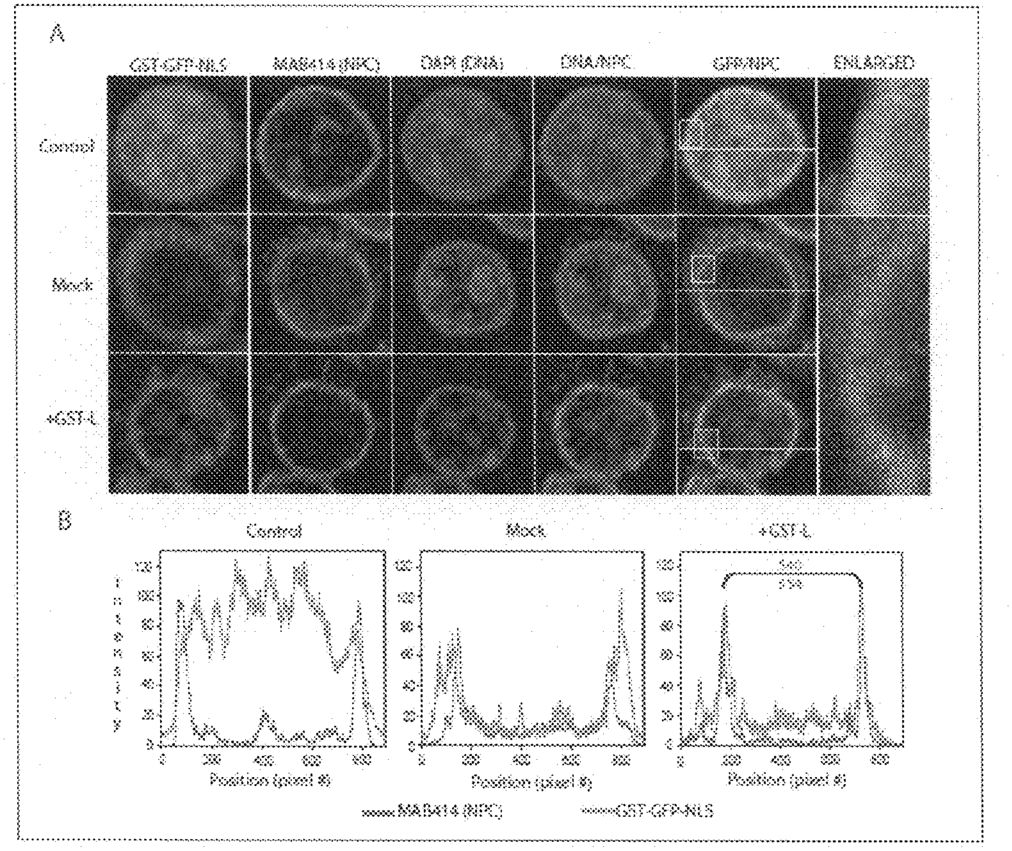
FIG. 9. Localization of cargo in L treated nuclei. Following standard import reactions, control, mock and GST-L treated samples were fixed and labeled with antibody Mab41 4, and DAP1 stain as described in Materials and Methods to label NPCs and DNA, respectively. (A) Confocal images of labeled nuclei following import were captured as described in Materials and Methods. DNA/NPC overlay images show the discrimination between the exterior and interior of the nuclear membrane in all samples. Overlay of cargo (GFP) and NPC signals show the different localization of cargo with each treatment. The yellow box indicates the section of the image enlarged at right. The yellow line represents the location of the line scan performed in B. (B) Intensity plots of cargo and NPC signals were constructed for lines dissecting treated nuclei. A smoothed 21 pixel-wide line scan was performed as described in the Materials and Methods on the images shown in A. to reveal the distribution of cargo near the nuclear envelope. Intensity of each signal was plotted versus its position on the line. The distance (in pixels) between the peaks of cargo and NPC signals in the GST-L treated sample is shown above and below the bracket, respectively.

Cargo is retained at the nuclear side of the NPC. The GFP fluorescence at the nuclear rim in nuclei treated with L suggested that import was interrupted while the cargo was traversing the NPC. If L affected the formation of a Ran gradient as suggested by our earlier experiments, one would not expect that accumulation would occur on the cytoplasmic side of the NPC since the trafficking of cargo through the pore is independent of Ran activity (Nakielny, S., and G. Dreyfuss. 1998. *Import and export of nuclear protein import receptor transportin by a mechanism independent of GTP hydrolysis. Curr. Biology* 8:89-95). Rather, the cargo should be arrested at the nuclear face, specifically at the terminal ring of the nuclear basket, where RanGTP mediates release of bound importinα/β-cargo complexes from the NPC and induces the export of the importins back into the cytoplasm (Shah, S., S. Tugendreich, and D. Forbes. 1998. *Major binding sites for the nuclear import receptor are the internal nucleoporin Nupl* 53 and the adjacent nuclear filament protein Tpr. J. Cell Biology 141:31-49). To determine if the cargo were docked on the inside or outside of the NPC we labeled the nuclei with DAP1 and antibody MAb 414, as an indicator for nuclear pore complexes, following import. Comparison of Mab41 4 (NPC) and DAPI (DNA) staining patterns showed that these experiments could distinguish between the inside and outside of the nuclear envelope as shown by the separation of red (NPC) and blue (DNA) signals in these images with overlapping areas observed as purple in color (FIG. 9A). Using this method, we compared the patterns of green (cargo) and red (NPC) fluorescence signals in control, mock, and L treated samples. In the control, we observed a red-yellow-green staining pattern from the outside to the inside of the nucleus suggesting, as expected, that the cargo was primarily on the inside. In mock import samples the reverse was true, with a green-yellow-red staining pattern observed due to the exclusion of the cargo from the nucleus. In L treated samples, a red-yellow-green pattern was also observed although the lack of a strong cargo staining in the interior of the nucleus and the close proximity of the cargo to the nuclear rim made this pattern less apparent.

To ascertain whether the relative distance between the NPC and cargo at the rim in L treated samples was consistent with localization at the nuclear basket of the NPC, we plotted the red (NPC) and green (cargo) signal intensity for lines dissecting the treated nuclei. In control and mock treated samples, no distinct peaks were observed overlapping the NPC label (FIG. 9B). Instead, the cargo signal changed gradually across these regions and was highest well away from the NPC peaks at the nuclear membrane. However, in the L treated sample the peaks of cargo fluorescence partially overlapped with the NPC signal at the nuclear periphery. These peaks were biased toward the interior of the nucleus. We determined the distance between the NPC and cargo peaks differed by approximately 19 pixels, 3.4% of the distance across the nucleus. If 10 μm is the approximate diameter of a nucleus, 3.4% is equivalent to 340 nm or roughly two times the distance from the cytosolic fibrils to the nuclear basket of a NPC (≈200 nm) (Nakielny, S., and G. Dreyfuss. 1998. *Import and export of nuclear protein import receptor transportin by a mechanism independent of GTP hydrolysis. Curr. Biology* 8:89-95).

Figure 10:
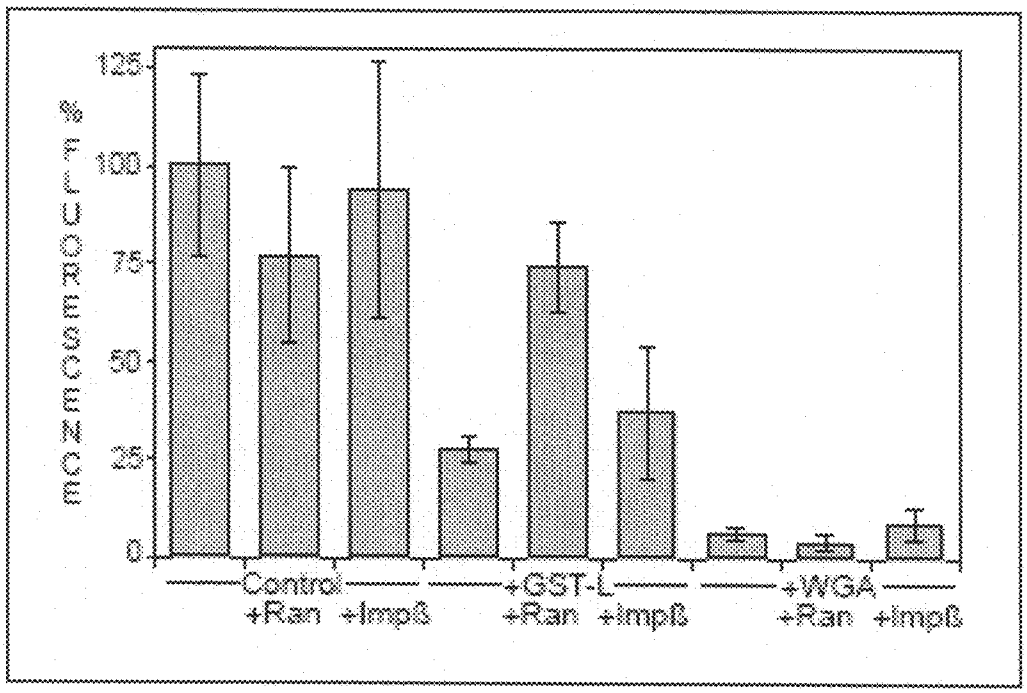
FIG. 10. Added Ran rescues import. Import reactions were performed in the absence or presence of 100 μg/ml GST-L with 100 μg/ml purified 6×His-wtRan, or 6×His-importin β or without added import factors as a control. Percent nuclear cargo accumulation versus the control was determined from the average intensity of GFP fluorescence as described in Example 2, Materials and Methods.

Addition of Ran rescues import in the presence of L. If L inhibited import solely by interacting with Ran and disrupting its gradient across the nuclear membrane, we predicted that addition of an excess of the protein should rescue import in the presence of L. This would leave some pool of Ran free of L and able to generate a RanGTP gradient needed for import. When purified recombinant wild-type Ran was added to import reactions in excess of the concentration of L, the amount of cargo in the nucleus increased to 80% of the control, rescuing import activity (FIG. 10). When we added a similar amount of importin β as a control, we observed little change in the nuclear accumulation of cargo in the presence of L. This sowed that specifically wt Ran, not any soluble import protein, was able to overcome the block induced by L.

Figure 11:
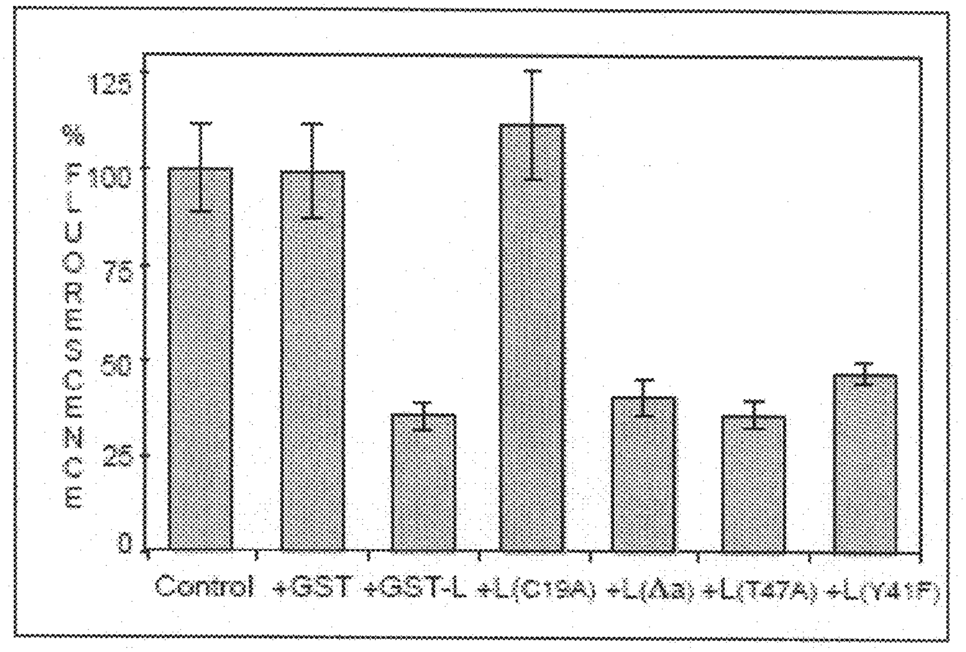
FIG. 11. Effects of L mutants on import. Import reactions were performed in the presence of GST, GST-L and GST-Lmutants (LΔa, L$C_{19}$A) at a concentration of 105 μg/ml. Percent nuclear cargo accumulation versus the control was determined from the average intensity of GFP fluorescence as described in Example 2, Materials and Methods.

Only L Zn-finger mutants do not inhibit import. L encodes zinc-finger and acidic domains that are important to its activity. Deletions of either domain or point mutations that replace zinc-coordinating residues lead to attenuated virus growth in cells with a competent interferon response (Dvorak, C. M. T., D. J. Hall, M. Hill, M. Riddle, A. Pranter, J. Dillman, M. Deibel, and A. C. Palmenberg. 2001. *Leader protein of encephalomyocarditis virus binds zinc, is phosphorylated during viral infection and affects the efficiency of genome translation. Virology* 290:261-71). Elimination of a putative phosphorylation site (Thr within the acidic domain also affects virus growth and efflux of nuclear proteins. These L mutants were also inactive when expressed alone in vivo. Only wild type inhibited export and expression of reporter mRNA (Porter, F. W., Y. Bochkov, A. J. Albee, C. Wiese, and A. C. Palmenberg. 2006. *A picornavirus protein disrupts nucleocytoplasmic transport by targeting Ran GTPase. Proc. Nat. Acad. Sci. USA* 103:12417-22). In contrast, an intact zinc-finger domain was sufficient to block Ran activity in in-vitro spindle assembly reactions. The reasons for this discrepancy are unclear. The possibilities include: 1) variations between the environment mammalian and *Xenopus* cells, 2) differences between L expressed in *E. coli* and mammalian systems, and 3) discrete requirements for inhibiting nucleocytoplasmic transport. To examine these possible scenarios, we tested recombinant L mutant fusion proteins with defective zinc-finger (GST-L $C_{19}$A) and acidic domains (GST-LΔa, GST-L $Y_{41}$F, GST-L $T_{47}$A) in our in vitro nuclear import assay. The zinc-finger mutant, L-$C_{19}$A lost all inhibitory activity and the acidic domain mutants had activity similar to wild-type L (FIG. 11). This suggests that in this in vitro reconstructed system, the zinc-finger of L alone is sufficient to inhibit both nuclear import and aster assembly and that outside of the cellular environment the acidic domain is not required.

Figure 12:
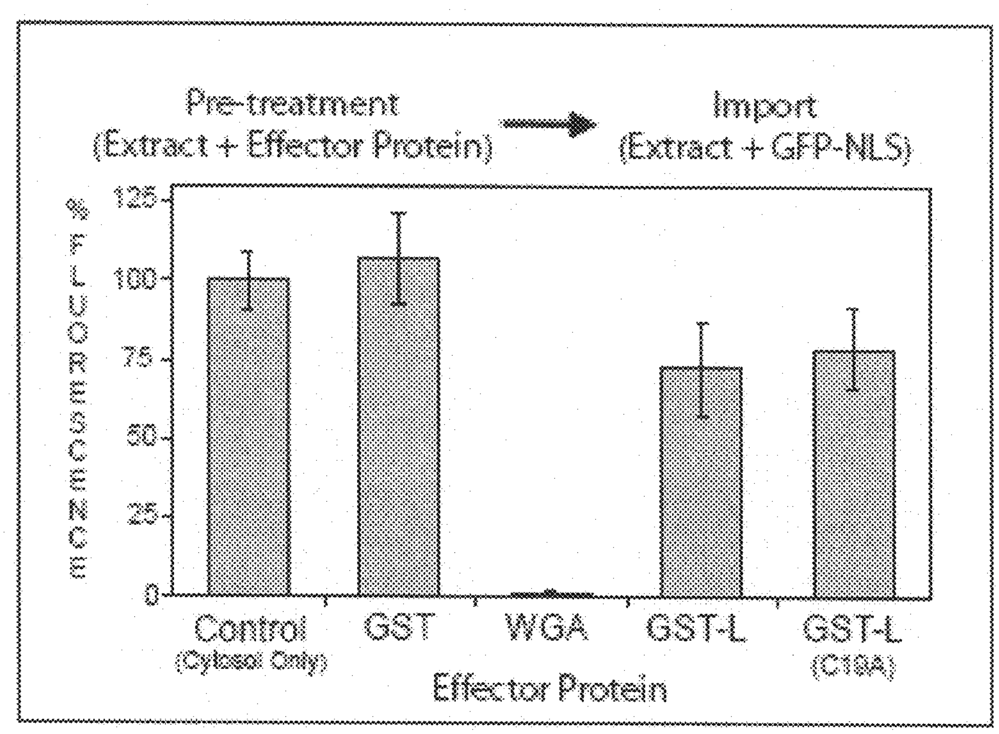
FIG. 12 Pre-treatment of nuclei with L does not inhibit import. Digitonin permeabilized cells were incubated with *Xenopus* cytosol and effector proteins in pre-import reactions for 35 minutes. Cells were then washed briefly with TB and standard import reactions were performed. Percent nuclear cargo accumulation versus the control was determined from the average intensity of GFP fluorescence as described in Example 2, Materials and Methods.

Pre-exposure to L does not inhibit import. Previous studies have shown that infection with the Mengo strain of EMCV leads to changes in NPC morphology (Lidsky, P. L., S. Hato, M. V. Bardina, A. G. Aminev, A. C. Palmenberg, E. V. Sheval, V. Y. Polyakov, F. J. van Kuppeveld, and V. Agol. 2006. *Nucleo-cytoplasmic traffic disorder induced by cardioviruses. J. Virology* 80:2705-17). This can be interpreted to suggest that like poliovirus 2Apro, L may permanently alter the trafficking capacity of NPCs in addition to inhibiting Ran function. To test for this possible effect, we pre-treated nuclei with L in *Xenopus* cytosol before assaying import activity. We postulated that if L bound, modified or degraded NPC components similar to VSV M protein or poliovirus 2Apro, pre-treatment should have a dramatic effect on import. Indeed, when digitonin treated cells were pre-treated with WGA, import was significantly inhibited (FIG. 12). In contrast, pre-treatment with L did not have a significant inhibitory effect. This shows that L does not permanently affect the import activity of NPC's and also suggests that the targeting of Ran is its most significant effect on import.

Discussion

In the experiments described here, we examined the effects of recombinant EMCV L in in-vitro reconstituted nuclear import assays. We showed that L rapidly and completely inhibited the nuclear accumulation of classical NLS-encoding cargo and that import activity could be restored by the addition of excess Ran. The rescue of import activity strongly supports the idea that L targets Ran. Ran-cycle defects that inhibit nuclear import have been successfully rescued in similar experiments both in-vivo and in-vitro (Clarkson, W. D., A. H. Corbett, B. M. Paschal, H. M. Kent, A. J. McCoy, L. Gerace, P. A. Silver, and M. Stewart. 1997. *Nuclear protein import is decreased by engineered mutants of nuclear transport factor* 2 (*NTF*2) *that do not bind GDP Ran. J. Mol. Biology* 272; 27). The L-induced cargo arrest at the interior of the NPC gives further support that it is Ran function, not the NPC or transport receptors themselves that is impinged by L since Ran GTP is critical for disassembly of import complexes and the release of cargo into the nucleus (Shah, S., S. Tugendreich, and D. Forbes. 1998. *Major binding sites for the nuclear import receptor are the internal nucleoporin Nupl* 53 *and the adjacent nuclear filament protein Tpr. J. Cell Biology* 141:31-49). While experiments are underway to determine whether this inner rim-localized cargo is indeed complexed with importins α/β at the nuclear basket, it is consistent with the localization of Nup 153, the high-affinity binding site for importin-cargo complexes on the interior of the NPC. Interestingly, this is one of the proteins cleaved by polioviruses and rhinoviruses that employ a 2Apro-dependent mechanism (Gustin, K. E., and P. Sarnow. 2001. *Effects of poliovirus infection on nucleo-cytoplasmic trafficking and nuclear pore complex composition. EMBO J.* 20:240-9). Thus, enteroviruses and cardioviruses may target the same step of import, the former blocking binding of importin-cargo complexes to their final binding site and the latter its release into the nucleus. In agreement with this hypothesis, a previous study showed that neither p62 or Nup153 are cleaved by cardioviruses (Lidsky, P. L., S. Hato, M. V. Bardina, A. G. Aminev, A. C. Palmenberg, E. V. Sheval, V. Y. Polyakov, F. J. van Kuppeveld, and V. Agol. 2006. *Nucleo-cytoplasmic traffic disorder induced by cardioviruses. J. Virology* 80:2705-17). However, this did not rule out effects elsewhere within the NPC. Importantly, here we also show that pre-exposing nuclei to L did not inhibit import once the soluble fraction was removed, indicating that L did not also permanently alter NPC structure. This may seem contradictory to published electron microscopy experiments that showed changes in NPCs upon infection with Mengovirus, a strain of EMCV (Lidsky, P. L., S. Hato, M. V. Bardina, A. G. Aminev, A. C. Palmenberg, E. V. Sheval, V. Y. Polyakov, F. J. van Kuppeveld, and V. Agol. 2006. *Nucleo-cytoplasmic traffic disorder induced by cardioviruses. J. Virology* 80:2705-17). However, loss of the central plug noted in this study is also consistent with absence of active transport. Several studies suggest that mRNA and proteins in-transit make up a significant portion of the central plug (Schafer, C., V. Shahin, L. Albermann, M. J. Hug, J. Reinhardt, H. Schillers, S. W. Schneider, and H. Oberleithner. 2002. *Aldosterone signalling across the nuclear envelope. Proc. Nat. Acad. Sci. USA* 99:7154-59; Stoffler, D., B. Feja, B. Fahrenkrog, J. Walz, D. Typke, and U. Aebi. 2003. *Cryo-electron tomography provides novel insights into nuclear pore architecture—implications for nucleocytoplasmic transport. J. Mol. Biology* 328:119-30). Thus, the loss of central plug density may simply be the result of transport shutoff.

Though it is currently unclear what step of Ran cycle is impeded by L, our preliminary studies indirectly suggest that it acts at the cytoplasmic face of the NPC. In EMCV infected cells, L is predominantly observed at the cytoplasmic periphery of the nucleus (Porter, F. W., Y. Bochkov, A. J. Albee, C. Wiese, and A. C. Palmenberg. 2006. *A picornavirus protein disrupts nucleocytoplasmic transport by targeting Ran GTPase. Proc. Nat. Acad. Sci. USA* 103:12417-22) and GST pulldown experiments have identified cytosolic ran associated protein, RanGAP1 but not the nuclear exchange factor, RCC1 among the co-precipitated proteins. A cytosolic mechanism may also explain why micromolar concentrations of L are required for robust activity in both of our *Xenopus* extract assay systems since Ran concentrations in these extracts are estimated to be in the low micromolar range (Clarke, P. R., C. Klebe, A. Wittinghofer, and E. Karsenti. 1995. *Regulation of Cdc2/cyclin B activation by Ran, a Ras-related GTPase. J. Cell Sci.* 108:1217-25). In contrast, Ran is highly enriched in the nucleoplasm of interphase cells (Bischoff, F. R., and H. Ponstingl. 1991. *Catalysis of guanine nucleotide exchange on Ran by the mitotic regulator RCC1. Nature* 354:80-82), so L many only encounter a fraction of that concentration at the cytoplasmic face of the NPC during EMCV infection. One confounding question raised by our previous experiments in *Xenopus* extracts was why only the zinc-finger domain was required to inhibit Ran cycling in this system while both the zinc finger and acidic domain were required in in-vivo expression and virus infection contexts (Dvorak, C. M. T., D. J. Hall, M. Hill, M. Riddle, A. Pranter, J. Dillman, M. Deibel, and A. C. Palmenberg. 2001. *Leader protein of encephalomyocarditis virus binds zinc, is phosphorylated during viral infection and affects the efficiency of genome translation. Virology* 290:261-71; Porter, F. W., Y. Bochkov, A. J. Albee, C. Wiese, and A. C. Palmenberg. 2006. *A picornavirus protein disrupts nucleocytoplasmic transport by targeting Ran GTPase. Proc. Nat. Acad. Sci. USA* 103:12417-22). Our results here show that again only the zinc-finger is required to maintain full activity. Previous reports have supported a role for both the zinc-finger and the acidic domain (specifically its phosphorylation sites) as critical for disrupting nuclear localization (Delhaye, S., V. van Pesch, and T. Michiels. 2004. *The leader protein of Theiler's virus interferes with nucleocytoplasmic trafficking of cellular proteins. J. Virology* 78:4357-62, Lidsky, P. L., S. Hato, M. V. Bardina, A. G. Aminev, A. C. Palmenberg, E. V. Sheval, V. Y. Polyakov, F. J. van Kuppeveld, and V. Agol. 2006. *Nucleo-cytoplasmic traffic disorder induced by cardioviruses. J. Virology* 80:2705-17). Our results here suggest that the acidic domain is only required in-vivo. It is possible that the acidic domain confers stability to L, giving it a long enough half-life to perform its function or it may target L to the nuclear periphery where it then has access to Ran and its cofactors. In-vivo expression experiments are currently underway to investigate these possibilities.

Although depletion of the Ran gradient can reasonably account for inhibition active import/export and the efflux of small (<40 kDa) proteins from the nucleus, it is likely that the role of L in this activity is more complex. The retrograde trafficking of rather large nuclear proteins (~100 kDa) in cardiovirus infected cells suggests that other changes have also occurred. The possibilities include; 1) that the exclusion limit of the pore has been increased, 2) the nuclear membrane has been compromised or 3) these proteins are being actively exported. How L might mediate these processes is unknown. One possibility is that a scrambled Ran gradient directly induces changes in the morphology of the soluble domains of Nups (Lyman, S. K., T. Guan, J. Bednenko, H. Wodrich, and L. Gerace. 2002. *Influence of cargo size on Ran and energy requirements for nuclear protein import. J. Cell Biology* 159:55-67) leading to an open channel that allows the diffusion of larger proteins out of the nucleus. Alternately, cyclin-dependent kinases may be involved. Cdk1 has been shown to induce reversible disassembly of Nups from NPC's in a phosphorylation-dependent mechanism (Onischenko, E. A., N. V. Gubanova, E. V. Kiseleva, and E. Hallberg. 2005. *Cdkl and okadaic acid-sensitive phosphatases control assembly of nuclear pore complexes in drosophila embryos. Mol Biol. Cell* 16:51 52-62). Interestingly, Lidsky et. al. have shown that CyclinB1, the binding partner of Cdk1, is trafficked to the nucleus during cardiovirus infection and that phosphorylation is somehow important for efflux (Lidsky, P. L., S. Hato, M. V. Bardina, A. G. Aminev, A. C. Palmenberg, E. V. Sheval, V. Y. Polyakov, F. J. van Kuppeveld, and V. Agol. 2006. *Nucleo-cytoplasmic traffic disorder induced by cardioviruses. J. Virology* 80:2705-17). Regardless of the mechanism, the disruption of nucleocytoplasmic trafficking by L is likely a critical component of the anti-host response in cardioviruses.

We claim:

1. A method of inhibiting Ran protein activity in at least one eukaryotic cell or cell-free extract, the method comprising:

(a) exposing an amino acid sequence comprising a purified full-length encephalomyocarditis virus (EMCV) leader protein (L protein) to at least one cell or cell-free extract in an amount effective to inhibit Ran activity in the cell or cell-free extract; and (b) evaluating Ran protein activity in the cell or cell-free extract.

2. The method of claim 1 wherein the sequence is selected from the group consisting of SEQ ID NOs: 1-8.

3. The method of claim 1 wherein the amino acid sequence is obtained from purified recombinant L protein.

4. The method of claim 1 wherein the sequence is obtained from a preparation of EMCV.

5. The method of claim 1 wherein step (b) comprises measuring the change in localization of cellular transport-specific proteins or RNA.

6. The method of claim 1 wherein step (b) comprises evaluating Ran inhibiting by measuring the ability of a cell-free extract to undergo Ran-dependent tubulin condensation into visible cellular spindle assemblies.

7. A method of inhibiting Ran protein activity in a eukaryotic cell, the method comprising administering to a patient in need thereof a therapeutically effective amount of an amino acid sequence comprising full-length encephalomyocarditis virus (EMCV) leader protein, and determining the effect of inhibiting Ran activity in the patient.

8. The method of claim 7 wherein the sequence is targeted to at least one specific cell type.

9. The method of claim 7 wherein the sequence is selected from the group consisting of SEQ ID NOs: 1-8.

10. A method of inhibiting Ran protein activity in at least one eukaryotic cell or cell-free extract, the method comprising:

(a) exposing an amino acid sequence comprising a modified full-length encephalomyocarditis virus (EMCV) leader protein (L protein) which has been purified to at least one cell or cell-free extract in an amount effective to inhibit Ran activity in the cell or cell-free extract, wherein said modification consists of deleting the acidic domain from the full-length protein; and (b) evaluating Ran protein activity in the cell or cell-free extract.

11. The method of claim 10 wherein the sequence to be modified is selected from the group consisting of SEQ ID NOs: 1-8.

* * * * *

UNITED STATES PATENT AND TRADEMARK OFFICE
CERTIFICATE OF CORRECTION

PATENT NO. : 7,741,022 B2
APPLICATION NO. : 11/654848
DATED : June 22, 2010
INVENTOR(S) : Frederick W. Porter et al.

It is certified that error appears in the above-identified patent and that said Letters Patent is hereby corrected as shown below:

Column 6, line 57 “picomaviruses” should be -- picornaviruses --
Column 18, line 24 “picomaviruses” should be -- picornaviruses --
Column 19, line 3 “picomaviruses” should be -- picornaviruses --
Column 19, line 50 “picomaviruses” should be -- picornaviruses --

Signed and Sealed this

Thirty-first Day of August, 2010

David J. Kappos
*Director of the United States Patent and Trademark Office*

UNITED STATES PATENT AND TRADEMARK OFFICE

CERTIFICATE OF CORRECTION

PATENT NO. : 7,741,022 B2
APPLICATION NO. : 11/654848
DATED : June 22, 2010
INVENTOR(S) : Frederick William Porter et al.

It is certified that error appears in the above-identified patent and that said Letters Patent is hereby corrected as shown below:

In the Specification

Column 1, Lines 15-18:
Delete the phrase:
"This invention was made with United States government support awarded by the following agencies: NIH, Grant Number AI07331; NSF, Grant Number 0344723. The United States government has certain rights in this invention."
And replace with:
--This invention was made with government support under AI017331 awarded by the National Institutes of Health and 0344723 awarded by the National Science Foundation. The government has certain rights in the invention.--.

Signed and Sealed this
Eighth Day of December, 2020

Andrei Iancu
*Director of the United States Patent and Trademark Office*

SEQUENCE LISTING

<160> NUMBER OF SEQ ID NOS: 17

<210> SEQ ID NO 1
<211> LENGTH: 67
<212> TYPE: PRT
<213> ORGANISM: Encephalomyocarditis virus

<400> SEQUENCE: 1

```
Met Ala Thr Thr Met Glu Gln Glu Thr Cys Ala His Ser Leu Thr Phe
1               5                   10                  15

Glu Glu Cys Pro Lys Cys Ser Ala Leu Gln Tyr Arg Asn Gly Phe Tyr
            20                  25                  30

Leu Leu Lys Tyr Asp Glu Glu Trp Tyr Pro Glu Glu Leu Leu Thr Asp
        35                  40                  45

Gly Glu Asp Asp Val Phe Asp Pro Glu Leu Asp Met Glu Val Val Phe
    50                  55                  60

Glu Leu Gln
65
```

<210> SEQ ID NO 2
<211> LENGTH: 67
<212> TYPE: PRT
<213> ORGANISM: Encephalomyocarditis virus

<400> SEQUENCE: 2

```
Met Ala Thr Thr Met Glu Gln Glu Thr Cys Ala His Ser Leu Thr Phe
1               5                   10                  15

Glu Glu Cys Pro Lys Cys Ser Ala Leu Gln Tyr Arg Asn Gly Phe Tyr
            20                  25                  30

Leu Leu Lys Tyr Asp Glu Glu Trp Tyr Pro Glu Glu Leu Leu Ile Asp
        35                  40                  45

Gly Glu Asp Asp Val Phe Asp Pro Glu Leu Asp Thr Glu Val Val Phe
    50                  55                  60

Glu Leu Gln
65
```

<210> SEQ ID NO 3
<211> LENGTH: 67
<212> TYPE: PRT
<213> ORGANISM: Encephalomyocarditis virus

<400> SEQUENCE: 3

```
Met Ala Thr Thr Met Glu Gln Glu Ile Cys Ala His Ser Leu Thr Leu
1               5                   10                  15

Lys Gly Cys Pro Lys Cys Ser Ala Leu Gln Tyr Arg Asn Gly Phe Tyr
            20                  25                  30

Leu Leu Lys Tyr Asp Glu Glu Trp Tyr Pro Glu Glu Leu Leu Thr Asp
        35                  40                  45

Gly Glu Asp Asp Val Phe Asp Pro Glu Leu Asp Met Glu Val Val Phe
    50                  55                  60

Glu Leu Gln
65
```

<210> SEQ ID NO 4
<211> LENGTH: 67
<212> TYPE: PRT
<213> ORGANISM: Encephalomyocarditis virus -continued

<400> SEQUENCE: 4

Met Ala Thr Thr Met Glu Gln Glu Ile Cys Ala His Ser Leu Thr Phe
1 5 10 15

Lys Gly Cys Pro Lys Cys Ser Ala Leu Gln Tyr Arg Asn Gly Phe Tyr
20 25 30

Leu Leu Lys Tyr Asp Glu Glu Trp Tyr Pro Glu Glu Leu Leu Thr Asp
35 40 45

Gly Glu Asp Asp Val Phe Asp Pro Glu Leu Asp Met Glu Val Val Phe
50 55 60

Glu Leu Gln
65

<210> SEQ ID NO 5
<211> LENGTH: 67
<212> TYPE: PRT
<213> ORGANISM: Encephalomyocarditis virus

<400> SEQUENCE: 5

Met Ala Thr Thr Met Glu Gln Glu Ile Cys Val His Ser Leu Ile Phe
1 5 10 15

Glu Glu Cys Pro Lys Cys Ser Ala Leu Gln Tyr Arg Asp Gly Phe Tyr
20 25 30

Leu Leu Arg Tyr Asp Glu Glu Trp Tyr Pro Gly Glu Leu Leu Thr Asp
35 40 45

Gly Glu Asp Asp Val Phe Asp Pro Glu Leu Asp Met Glu Val Val Phe
50 55 60

Glu Leu Gln
65

<210> SEQ ID NO 6
<211> LENGTH: 67
<212> TYPE: PRT
<213> ORGANISM: Encephalomyocarditis virus

<400> SEQUENCE: 6

Met Ala Thr Thr Met Glu Gln Glu Ile Cys Ala His Ser Met Thr Phe
1 5 10 15

Glu Glu Cys Pro Lys Cys Ser Ala Leu Gln Tyr Arg Asn Gly Phe Tyr
20 25 30

Leu Leu Lys Tyr Asp Glu Glu Trp Tyr Pro Glu Glu Leu Leu Thr Asp
35 40 45

Gly Glu Asp Asp Val Phe Asp Pro Asp Leu Asp Met Glu Val Val Phe
50 55 60

Glu Thr Gln
65

<210> SEQ ID NO 7
<211> LENGTH: 67
<212> TYPE: PRT
<213> ORGANISM: Encephalomyocarditis virus

<400> SEQUENCE: 7

Met Ala Thr Thr Met Glu Gln Glu Ile Cys Ala His Ser Met Thr Phe
1 5 10 15

Glu Glu Cys Pro Lys Cys Ser Ala Leu Gln Tyr Arg Asn Gly Phe Tyr
20 25 30

Leu Leu Lys Tyr Asp Glu Glu Trp Tyr Pro Glu Glu Ser Leu Thr Asp
35 40 45

-continued

Gly Glu Asp Asp Val Phe Asp Pro Asp Leu Asp Met Glu Val Val Phe
    50                  55                  60

Glu Thr Gln
65

<210> SEQ ID NO 8
<211> LENGTH: 67
<212> TYPE: PRT
<213> ORGANISM: Encephalomyocarditis virus

<400> SEQUENCE: 8

Met Ala Thr Thr Met Glu Gln Glu Ile Cys Ala His Ser Met Thr Phe
1               5                   10                  15

Glu Glu Cys Pro Lys Cys Ser Ala Leu Gln Tyr Arg Asn Gly Phe Tyr
            20                  25                  30

Leu Leu Lys Tyr Asp Glu Glu Trp Tyr Pro Glu Glu Leu Leu Thr Asp
        35                  40                  45

Gly Glu Asp Asp Val Phe Asp Pro Asp Leu Asp Ile Glu Val Val Phe
    50                  55                  60

Glu Thr Gln
65

<210> SEQ ID NO 9
<211> LENGTH: 76
<212> TYPE: PRT
<213> ORGANISM: Theiler's encephalomyelitis virus

<400> SEQUENCE: 9

Met Ala Cys Lys His Gly Tyr Pro Asp Val Cys Pro Ile Cys Thr Ala
1               5                   10                  15

Ile Asp Val Thr Pro Gly Phe Glu Tyr Leu Leu Leu Ala Asp Gly Glu
            20                  25                  30

Trp Phe Pro Thr Asp Leu Leu Cys Val Asp Leu Asp Asp Asp Val Phe
        35                  40                  45

Trp Pro Ser Asp Ser Ser Asn Gln Ser Ala Thr Met Glu Trp Thr Asp
    50                  55                  60

Ile Pro Leu Ile Cys Asp Thr Val Met Glu Pro Gln
65                  70                  75

<210> SEQ ID NO 10
<211> LENGTH: 76
<212> TYPE: PRT
<213> ORGANISM: Theiler's encephalomyelitis virus

<400> SEQUENCE: 10

Met Ala Cys Lys His Gly Tyr Pro Asp Val Cys Pro Ile Cys Thr Ala
1               5                   10                  15

Val Asp Ala Thr Pro Asp Phe Glu Tyr Leu Leu Met Ala Asp Gly Glu
            20                  25                  30

Trp Phe Pro Thr Asp Leu Leu Cys Val Asp Leu Asp Asp Asp Val Phe
        35                  40                  45

Trp Pro Ser Asp Thr Ser Thr Gln Pro Ala Thr Met Glu Trp Thr Asp
    50                  55                  60

Val Pro Leu Val Cys Asp Thr Val Met Glu Pro Gln
65                  70                  75

<210> SEQ ID NO 11
<211> LENGTH: 76

-continued

```
<212> TYPE: PRT
<213> ORGANISM: Theiler's encephalomyelitis virus

<400> SEQUENCE: 11

Met Ala Cys Lys His Gly Tyr Pro Asp Val Cys Pro Ile Cys Thr Ala
1               5                   10                  15

Val Asp Val Thr Pro Gly Phe Glu Tyr Leu Leu Leu Ala Asp Gly Glu
            20                  25                  30

Trp Phe Pro Thr Asp Leu Leu Cys Val Asp Leu Asp Asp Asp Val Phe
        35                  40                  45

Trp Pro Ser Asn Ser Ser Asn Gln Ser Glu Thr Met Glu Trp Thr Asp
    50                  55                  60

Leu Pro Leu Val Arg Asp Ile Val Met Glu Pro Gln
65                  70                  75


<210> SEQ ID NO 12
<211> LENGTH: 76
<212> TYPE: PRT
<213> ORGANISM: Theiler's encephalomyelitis virus

<400> SEQUENCE: 12

Met Ala Cys Lys His Gly Tyr Pro Asp Val Cys Pro Ile Cys Thr Ala
1               5                   10                  15

Val Asp Ala Thr Pro Asp Phe Glu Tyr Leu Leu Met Ala Asp Gly Glu
            20                  25                  30

Trp Tyr Pro Thr Asp Leu Leu Cys Val Asp Leu Asp Asp Asp Val Phe
        35                  40                  45

Trp Pro Ser Asp Thr Ser Asn Gln Ser Ala Thr Met Asp Trp Thr Asp
    50                  55                  60

Val Pro Leu Ile Arg Asp Ile Val Met Glu Pro Gln
65                  70                  75


<210> SEQ ID NO 13
<211> LENGTH: 76
<212> TYPE: PRT
<213> ORGANISM: Theiler's encephalomyelitis virus

<400> SEQUENCE: 13

Met Ala Cys Ile His Gly Tyr Pro Ser Val Cys Pro Ile Cys Thr Ala
1               5                   10                  15

Ile Asp Lys Ser Ser Asp Gly Met Tyr Leu Leu Leu Ala Asp Asn Glu
            20                  25                  30

Trp Phe Pro Ala Asp Leu Leu Thr Met Asp Leu Asp Asp Asp Val Phe
        35                  40                  45

Trp Pro Asn Asp Glu Ser Asp Val Ser Glu Thr Met Asp Trp Thr Asp
    50                  55                  60

Leu Pro Phe Ile Leu Asp Thr Ile Met Glu Pro Gln
65                  70                  75


<210> SEQ ID NO 14
<211> LENGTH: 21
<212> TYPE: PRT
<213> ORGANISM: Encephalomyocarditis virus
<220> FEATURE:
<221> NAME/KEY: MISC_FEATURE
<222> LOCATION: (3)..(3)
<223> OTHER INFORMATION: X AT POSITION 3 CAN BE I OR T
<220> FEATURE:
<221> NAME/KEY: MISC_FEATURE
<222> LOCATION: (5)..(5)
<223> OTHER INFORMATION: X AT POSITION 5 CAN BE A OR V
```

-continued

```
<220> FEATURE:
<221> NAME/KEY: MISC_FEATURE
<222> LOCATION: (8)..(8)
<223> OTHER INFORMATION: X AT POSITION 8 CAN BE L OR M
<220> FEATURE:
<221> NAME/KEY: MISC_FEATURE
<222> LOCATION: (11)..(11)
<223> OTHER INFORMATION: X AT POSITION 11 CAN BE E OR K
<220> FEATURE:
<221> NAME/KEY: MISC_FEATURE
<222> LOCATION: (12)..(12)
<223> OTHER INFORMATION: X AT POSITION 12 CAN BE E OR G

<400> SEQUENCE: 14

Met Ala Xaa Cys Xaa His Ser Xaa Thr Phe Xaa Xaa Cys Pro Lys Cys
1               5                   10                  15

Ser Ala Leu Gln Tyr
            20


<210> SEQ ID NO 15
<211> LENGTH: 19
<212> TYPE: PRT
<213> ORGANISM: Theiler's encephalomyelitis virus
<220> FEATURE:
<221> NAME/KEY: MISC_FEATURE
<222> LOCATION: (4)..(4)
<223> OTHER INFORMATION: X AT POSITION 4 CAN BE I OR K
<220> FEATURE:
<221> NAME/KEY: MISC_FEATURE
<222> LOCATION: (9)..(9)
<223> OTHER INFORMATION: X AT POSITION 9 CAN BE D OR S
<220> FEATURE:
<221> NAME/KEY: MISC_FEATURE
<222> LOCATION: (17)..(17)
<223> OTHER INFORMATION: X AT POSITION 17 CAN BE I OR V
<220> FEATURE:
<221> NAME/KEY: MISC_FEATURE
<222> LOCATION: (19)..(19)
<223> OTHER INFORMATION: X AT POSITION 19 CAN BE A OR V OR K

<400> SEQUENCE: 15

Met Ala Cys Xaa His Gly Tyr Pro Xaa Val Cys Pro Ile Cys Thr Ala
1               5                   10                  15

Xaa Asp Xaa


<210> SEQ ID NO 16
<211> LENGTH: 42
<212> TYPE: PRT
<213> ORGANISM: Encephalomyocarditis virus

<400> SEQUENCE: 16

Met Ala Thr Thr Met Glu Gln Glu Thr Cys Ala His Ser Leu Thr Phe
1               5                   10                  15

Glu Glu Cys Pro Lys Cys Ser Ala Leu Gln Tyr Arg Asn Gly Phe Tyr
            20                  25                  30

Leu Leu Lys Tyr Val Val Phe Glu Leu Gln
        35                  40


<210> SEQ ID NO 17
<211> LENGTH: 54
<212> TYPE: PRT
<213> ORGANISM: Encephalomyocarditis virus

<400> SEQUENCE: 17

Met Ala Thr Thr Met Glu Gln Glu Thr Ser Ala Leu Gln Tyr Arg Asn
1               5                   10                  15
```

-continued

```
Gly Phe Tyr Leu Leu Lys Tyr Asp Glu Glu Trp Tyr Pro Glu Glu Leu
            20                  25                  30

Leu Thr Asp Gly Glu Asp Asp Val Phe Asp Pro Glu Leu Asp Met Glu
        35                  40                  45

Val Val Phe Glu Leu Gln
    50
```